US008367808B2

(12) United States Patent
Elsemore et al.

(10) Patent No.: US 8,367,808 B2
(45) Date of Patent: Feb. 5, 2013

(54) METHODS, DEVICES, KITS AND COMPOSITIONS FOR DETECTING WHIPWORM

(75) Inventors: David Allen Elsemore, South Portland, ME (US); Laurie A. Flynn, Raymond, ME (US); Michael Crawford, St. Louis, MO (US)

(73) Assignees: IDEXX Laboratories, Inc., Westbrook, ME (US); Divergence, Inc., St. Louis, MO (US)

( * ) Notice: Subject to any disclaimer, the term of this patent is extended or adjusted under 35 U.S.C. 154(b) by 0 days.

(21) Appl. No.: 13/182,585

(22) Filed: Jul. 14, 2011

(65) Prior Publication Data

US 2012/0208983 A1 Aug. 16, 2012

Related U.S. Application Data

(62) Division of application No. 12/467,794, filed on May 18, 2009, now Pat. No. 7,993,861.

(60) Provisional application No. 61/128,077, filed on May 19, 2008.

(51) Int. Cl.
*C07K 16/00* (2006.01)
*A61K 39/395* (2006.01)
(52) U.S. Cl. ............... 530/388.6; 530/387.3; 530/387.9; 530/389.1; 424/135.1; 424/141.1; 424/151.1
(58) Field of Classification Search .................. None
See application file for complete search history.

(56) References Cited

U.S. PATENT DOCUMENTS

| | | | |
|---|---|---|---|
| 4,322,495 A | 3/1982 | Kato | |
| 4,756,908 A | 7/1988 | Lew | |
| 4,789,631 A | 12/1988 | Maggio | |
| 4,839,275 A | 6/1989 | Weil | |
| 4,978,504 A | 12/1990 | Nason | |
| 5,078,968 A | 1/1992 | Nason | |
| 5,238,649 A | 8/1993 | Nason | |
| 5,266,266 A | 11/1993 | Nason | |
| 5,726,010 A | 3/1998 | Clark | |
| 5,753,787 A | 5/1998 | Hawdon et al. | |
| 5,843,706 A | 12/1998 | Cobon et al. | |
| 5,882,943 A | 3/1999 | Aldeen | |
| 6,057,166 A | 5/2000 | Childs et al. | |
| 6,391,569 B1 | 5/2002 | Grieve et al. | |
| 6,596,502 B2 | 7/2003 | Lee | |
| 7,303,752 B2 | 12/2007 | Hotez et al. | |
| 7,736,660 B2 | 6/2010 | Elsemore et al. | |
| 2002/0132270 A1 | 9/2002 | Lee | |
| 2003/0129680 A1 | 7/2003 | O'Connor, Jr. | |
| 2003/0202980 A1 | 10/2003 | Caplan et al. | |
| 2004/0014087 A1 | 1/2004 | Hodgson et al. | |
| 2004/0214244 A1 | 10/2004 | Tonelli et al. | |
| 2005/0042232 A1 | 2/2005 | Hotez et al. | |
| 2006/0198844 A1 | 9/2006 | Langenfeld | |
| 2007/0053920 A1 | 3/2007 | Heath et al. | |
| 2008/0033148 A1 | 2/2008 | Xu et al. | |
| 2008/0108793 A1 | 5/2008 | Berman et al. | |
| 2008/0311557 A1 | 12/2008 | Elsemore et al. | |
| 2008/0311600 A1 | 12/2008 | Elsemore et al. | |
| 2009/0286228 A1 | 11/2009 | Elsemore et al. | |
| 2009/0286229 A1 | 11/2009 | Elsemore et al. | |
| 2009/0286230 A1 | 11/2009 | Elsemore et al. | |
| 2009/0286231 A1 | 11/2009 | Elsemore et al. | |
| 2010/0151500 A1 | 6/2010 | Geng et al. | |

FOREIGN PATENT DOCUMENTS

| | | |
|---|---|---|
| WO | 98/12563 | 3/1998 |
| WO | 02/75313 A1 | 9/2002 |
| WO | 03/032917 | 4/2003 |
| WO | 2004/064864 | 8/2004 |
| WO | 2004/097412 A2 | 11/2004 |
| WO | 2006/135799 | 12/2006 |
| WO | 2008/156650 | 12/2008 |
| WO | 2009/143080 | 11/2009 |
| WO | 2009/143083 | 11/2009 |

OTHER PUBLICATIONS

GenBank Accession No. CB189370. Feb. 5, 2003. [Retrieved from the Internet Mar. 30, 2010: <URL:http://ncbi.nlm.nih.gov/nucest/28252762>].
GenBank Accession No. BQ089025. Apr. 5, 2002. [Retrieved from the Internet Mar. 30, 2010: <URL:http://ncbi.nlm.nih.gov/nucest/20063226>].
GenBank Accession No. BM966041. Mar. 20, 2002. [Retrieved from the Internet Mar. 30, 2010: <URL:http://ncbi.nlm.nih.gov/nucest/19558790>].
GenBank Accession No. BQ088880. Apr. 5, 2002. [Retrieved from the Internet Mar. 30, 2010: <URL:http://ncbi.nlm.nih.gov/nucest/20063081>].
Uniprot submission P19398. Nov. 1, 1990. [Retrieved from the Internet Mar. 30, 2010: <URL: http://www.uniprot.org/uniprot/P19398>).
Uniprot submission O77416. May 16, 2003. [Retrieved from the Internet Mar. 30, 2010: <URL: http://www.uniprot.org/uniprot/O77416>].
Uniprot submission Q2VMT7. Jan. 10, 2006. [Retrieved from the Internet Mar. 30, 2010: <URL: http://www.uniprot.org/uniprot/Q2VMT7>].
Uniprot submission Q9U6V1. May 1, 2000. [Retrieved from the Internet Mar. 30, 2010: <URL: http://www.uniprot.org/uniprot/Q9U6V1>].
Uniprot submission Q16938. Nov. 1, 1996. [Retrieved from the Internet Mar. 30, 2010: <URL: http://www.uniprot.org/uniprot/Q16938>].

(Continued)

*Primary Examiner* — Padma Baskar
(74) *Attorney, Agent, or Firm* — McDonnell Boehnen Hulbert & Berghoff LLP

(57) ABSTRACT

Methods, devices, kits and compositions for detecting the presence or absence of whipworm in a fecal sample are disclosed herein. The methods, devices, kits and compositions of the present invention may be used to confirm the presence or absence of whipworm in a fecal sample from a mammal that may also be infected with one or more of hookworm, roundworm, and heartworm. Confirmation of the presence or absence of whipworm in the mammal may be made, for example, for the purpose of selecting an optimal course of treating the mammal and/or for the purpose of determining whether the mammal has been rid of the infection after treatment has been initiated.

10 Claims, 14 Drawing Sheets

OTHER PUBLICATIONS

Uniprot submission Q962V8. Dec. 1, 2001. [Retrieved from the Internet Mar. 30, 2010: <URL: http://www.uniprot.org/uniprot/Q962V8>].

Ambler, et al., "Biological Techniques for Studying the Allergenic Components of Nematodes. I. Detection of Allergenic Components in *Ascaris suum* Extracts", J. Immunol. Methods, vol. 1, No. 4, pp. 317-327, (1972).

Britton, et al., "Extensive diversity in repeat unit sequences of the cDNA encoding the polyprotein antigen/allergen from the bovine lungworm *Dictyocaulus viviparous*", Mol. Biochem. Parasitol. vol. 72, pp. 77-88, (1995).

Christie, et al., "The ABA-1 allergen of the nematode *Ascaris suum*: epitope stability, mass spectrometry, and N-terminal sequence comparison with its homologue in *Toxocara canis*", Clin. Exp. Immunol., vol. 92, pp. 125-132, (1993).

Kennedy, "Stage-specific secreted antigens of the parasitic larval stages of the nematode *Ascaris*" Immunology, vol. 58, No. 3, pp. 515-22, (1986).

McGibbon, et al., "Identification of the major *Ascaris* allergen and its purification to homogeneity by high-performance liquid chromatography", Mot Biochem. Parasitol., vol. 39, No. 2, pp. 163-172, (1990).

Meenan, et al., "Resonance assignment of ABA-1A, from *Ascaris suum* nematode polyprotein allergen", J. Biomol. NMR, vol. 32, No. 2 p. 176, (2005).

Poole, et al., "Cloning of a cuticular antigen that contains multiple tandem repeats from the filarial parasite *Dirofilaria immitis*", Proc. Natl. Acad. Sci. USA, vol. 89, No. 13, pp. 5986-5990, (1992).

Solovyova, et al., "The polyprotein and FAR lipid binding proteins of nematodes: shape and monomer/dimer states in ligand-free and bound forms", Eur. Biophys. J., vol. 32, No. 5, pp. 465-476, (2003).

Spence, et al., "A cDNA encoding repeating units of the ABA-1 allergen of *Ascaris*", Mol. Biochem. Parasitol. vol. 57, pp. 339-343, (1993).

The *C. elegans* Sequencing Consortium, et al., "Genome Sequence of the Nematode *C. elegans*: A Platform for Investigating Biology", Science, vol. 282, pp. 2012-2018, (1998).

Tweedie, et al., "*Brugia pahangi* and *Brugia malayi*: a surface-associated glycoprotein (gp15/400) is composed of multiple tandemly repeated units and processed from a 400-kDa precursor", Exp. Parasitol., vol. 76, No. 2, pp. 156-164, (1993).

Westermarck, et al., "Faecal hydrolase activity as determined by radial enzyme diffusion: a new method for detecting pancreatic dysfunction in the dog", Res. Vet. Sci., vol. 28, No. 3, pp. 341-346, (1980) (Abstract).

Williams, et al., "Comparison of methods for assay of the fecal proteolytic activity", Vet. Clin. Pathol, vol. 19, No. 1, pp. 20-24, (1990) (Abstract).

Williams, et al., "Fecal proteolytic activity in clinically normal cats and in a cat with exocrine pancreatic insufficiency", J. Am. Vet. Med. Assoc., vol. 197, No. 2, pp. 1112-1113, 1116, (1990) (Abstract).

Babin, et al., "The Isoinhibitors of Chymotrypsin/Elastase from *Ascaris lumbricoides*: The Primary Structure", Archives of Biochemistry and Biophysics, vol. 232, No. 1, pp. 143-161, (1984).

Cappello, et al., "*Ancylostoma caninum* anticoagulant peptide: A hookworm-derived inhibitor of human coagulation factor Xa", Proc. Natl. Acad. Sci., vol. 92, pp. 6152-6156, (1995).

Ford, et al., "Characterization of a Novel Filarial Serine Protease Inhibitor, Ov-SPI-1, from *Onchocerca volvulus*, with Potential Multifunctional Roles during Development of the Parasite", J. of Biol. Chem., vol. 280, No. 49, pp. 40845-40856, (2005).

Fraefel, et al "The amino acid sequence of a trypsin inhibitor isolated from *Ascaris (Ascaris lumbricoides* var. *suum)*", . Biochim. Biophys. Acta, vol. 154, pp. 615-617, (1968).

Goodman, et al., "Isolation of the Trypsin Inhibitors in *Ascaris lumbricoides* var. *suum* Using Affinity Chromatography", Analytical Biochemistry, vol. 120, pp. 387-393 (1982).

Grasberger, et al., "High-resolution structure of *Ascaris* trypsin inhibitor in solution: direct evidence for a pH-induced conformational transition in the reactive site", Structure, vol. 2, No. 7, pp. 669-678, (1994).

Gronenborn, et al., "Sequential resonance assignment and secondary structure determination of the *Ascaris* trypsin inhibitor, a member of a novel class of proteinase inhibitors", Biochemistry, vol. 29, No. 1, pp. 1183-189, (1990).

Harrison, et al., "Molecular Characterization of *Ancylostoma* Inhibitors of Coagulation Factor Xa", J. of Biol. Chem., vol. 277, No. 8, pp. 6223-6229, (2002).

Hawley, et al., "*Ascaris suum*: Are Trypsin Inhibitors Involved in Species Specificity of Ascarid Nematodes?", Experimental Parasitology, vol. 75, pp. 112-118 (1992).

Huang, et al., "The molecular structure of the complex of *Ascaris* chymotrypsin/elastase inhibitor with porcine elastase", Structure, vol. 2, No. 7, pp. 679-689, (1994).

Lu, et al., "*Anisakis simplex*: Mutational Bursts in the Reactive Site Centers of Serine Protease Inhibitors from an Acarid Nematode", Experimental Parasitology, vol. 89, pp. 257-261, (1998).

Martzen, et al., "*Ascaris suum*: Localization by Immunochemical and Fluorescent Probes of Host Proteases and Parasite Proteinase Inhibitors in Cross-sections", Experimental Parasitology, vol. 60, pp. 139-149, (1985).

Nguyen, et al., "Expression and characterization of elastase inhibitors from the ascarid nematodes *Anisakis simplex* and *Ascaris suum*", Mol. Biochem. Parasitology, vol. 102, pp. 79-89, (1999).

Peanasky, et at "The Isoinhibitors of Chymotrypsin/Elastase from *Ascaris lumbricoides*: Isolation by Affinity Chromatography and Association with the Enzymes", Archives of Biochemistry and Biophysics, vol. 232, No. 1, pp. 127-134, (1984).

Rhoads, et al., "*Trichuris suis*: A Secretory Serine Protease Inhibitor", Experimental Parasitology, vol. 94, pp. 1-7, (2000).

Rhoads, et al., "*Trichuris suis*: A Secretory Chymotrypsin/Elastase Inhibitor with Potential as an Immunomodulator", Experimental Parasitology, vol. 95, pp. 36-44, (2000).

Stanssens, et al., "Anticoagulant repertoire of the hookworm *Ancylostoma caninum*", Proc. Natl. Acad. Sci., vol. 93, pp. 2149-2154, (1996).

Uniprot submission P07851. Aug. 1988. [Retrieved from the internet Dec. 13, 2009: URL:http://www.uniprotorg/uniprot/P078511 in entirety.

Uniprot Submission P91811. May 1997 [Retrieved from the internet Nov. 7, 2009].

Uniport submission 044397. Jun. 1988 [Retrieved from the internet Nov. 11, 2009: [<URL:http://www.uniport.org/uniport/044397>].

Bailey, "The Raising of a Polyclonal Antiserum to a Protein", Methods Mol. Biol., vol. 32, pp. 381-388, (1994).

Dean, "Preparation and Characterization of Monoclonal Antibodies to Proteins and Other Cellular Components", Methods Mol. Biol., vol. 32, pp. 361-379, 1994 (Abstract).

Dean, "Preparation and Testing of Monoclonal Antibodies to Recombinant Proteins", Methods Mol. Biol., vol. 80, pp. 23-37, (1998).

Drenckhanhn, et al., "Production of Polyclonal Antibodies against Proteins and Peptides", Methods Cell Biol., vol. 37, pp. 7-56, (1993).

Dryden, et al., "Comparison of Common Fecal Flotation Techniques for the Recovery of Parasite Eggs and Oocysts", Vet. Ther., vol. 6, No. 1, pp. 15-28, (2005).

Gullick, "Production of Antisera to Synthetic Peptides", Methods Mol. Biol., vol. 32, pp. 389-399, (1994).

Kennedy, "The Nematode Polyprotein Allergens/Antigens", Parasitol. Today, vol. 16, No. 9, pp. 373-380, (2000).

Memoranda, "Parasite Antigens", Bull. World Health Organ, vol. 52, pp. 237-249, (1975).

Morrison, "In Vitro Antibodies: Strategies for Production and Application", Annu. Rev. Immunol., vol. 10, pp. 239-265, (1992).

Prociv et al., "Human enteric infection with *Ancyostoma caninum*: hookworms reappraised in the light of a "new" zoonosis", Acta. Tropica., vol. 62, pp. 23-44, (1996).

Wright, et al., "Genetically Engineered Antibodies: Progress and Prospects", Grit. Rev. Immunol., vol. 12 (3-4), pp. 125-168, (1992).

Xia, et al "The ABA-1 allergen of *Ascaris lumbricoides*: sequence polymorphism stage and tissue-specific expression, lipid binding function and protein biophysical properties", Parasitology, vol. 120 (Pt.2), pp. 211-224, (2000).

Yahiro, et al., "Identification, characterization and expression of *Toxocara canis* nematode polyprotein allergen TBA-1", Parasite Immunol., vol. 20, No. 8, pp. 351-357, (1998).

NCBI Blast: SEQ IS No. 4 (Performed Aug. 27, 2009 using http://blast.ncbi.nlm.nih.gov/blast.cgi).

Abdel-Rahman et al., Evaluation of a diagnostic monoclonal antibody-based capture enzyme-linked immunosorbent assay for detection of a 26- to 28-kd *Fasciola hepatica* coproantigen in cattle, American Journal of Veterinary Research 59:533-537 (1998).

Bungiro, et al., "Detection of Excretory/Secretory Coproantigens in Experimental in Hookworm infection," Am. J. Trop. Med. Hyg. 73(5):915-920 (2005).

Bungiro, Jr., et al., "Purification and Molecular Cloning of and Immunization with *Ancylostoma ceylancium* Excretory-Secretory Protein 2, an Immunocreactive Immunoreactive Protein Produced by Adult Hookworms," Infection and Immunity 72(4):2203-2213 (2004).

Carleton et al., "Prevalence of *Dirofilaria immitis* and gastrointestinal helminths in cats euthanized at animal control agencies in northwest Georgia," Veterinary Parasitology 119:319-326 (2004).

Coulaud, J.P., et al., "Albendazole: a new single dose anthelmintic," Study in 1455 patients, Acta Tropica 41:87-90 (1984).

De Oliveira et al., "IgM-ELISA for diagnosis of *Schistosomiasis mansoni* in low endemic areas," Cadernos de saude publica / Ministerio da Saude, Fundacao Oswaldo Cruz, Escola Nacional de Saude Publica 19:255-261 (2003).

Deplazes et al., "Detection of *Taenia hydatigena* copro-antigens by ELISA in dogs," Veterinary Parisitology 36:91-103 (1990).

Dumenigo et al., "Kinetics of antibody-based antigen detection in serum and faeces of sheep experimentally infected with *Fasciola hepatica*," Veterinary Parasitology 86:23-31 (1999).

Foreyt, W.J., "Veterinary Parasitology Reference Manual," Fifth Edition, 2001, ISBN 0-8138-2419-2, pp. 3-10.

Hill et al., "A *Trichuris* specific diagnostic antigen from culture fluids of *Trichuris suis* adult worms", Veterinary Parasitology, vol. 68, pp. 91-102, (1997).

Idexx Laboratories Canine Parvovirus Antigen Test Kit package insert (English Section Only), 2012.

Martinez-Maya et al., "Taeniosis and detection of antibodies against Cysticeri among inhabitants 4 a rural community in Guerro State, Mexico," Salud Publica de Mexico 45:84-89 (2003).

Ott et al., "Demonstration of both immunologically unique and common antigenic determinants in *Dirofilaria immitis* and *Toxocara canis* using monoclonal antibodies," Veterinary Immunology and Immunopathology 10:147-153 (1985).

Roberts, L.S., et al., "Foundations of Parasitology," Fifth Edition, 1996, Library of Congress Card Catalog No. 94-72939, ISBN 0-697-26071-2, pp. 1-4.

Southworth, D., Exine development in Gerbera JamesonlI (Asteraceae: Mutisieae), American Journal of Botany, 70:1038-1047 (1983).

Voller, Allster, "The Enzyme Linked Immunosorbent Assay", Diagnostic Horizon, vol. 2, No. 1, pp. 1-7, Feb. 1978.

Willard et al., "Diagnosis of *Aelurostrongylus abstrusus* and *Dirofilaria immitis* infections in cats from a humane shelter," Journal of the American Veterinary Medical Association 192:913-916 (1988).

Yamasaki, et al., "Development of Highly Specific Recombinant *Toxocara canis* Second-Stage Larva Excretory-Secretory Antigen for Immunodiagnosis of Human Toxocariasis," Journal of Clinical Microbiology 38 (4):1409-1413 (2000).

Zhan et atl., "Molecular characterisation of the Ancylostoma-secreted protein family from the adult stage of *Ancylostoma caninum*," International Journal for Parasitology 33:897-907 (2003).

Houghten, Richard A., et al., "Relative Importance of Position and Individual Amino Acid Residues in Peptide Antigen-Antibody Interactions: Implications in the Mechanism of Antigenic Drift and Antigenic Shift," Vaccines, 1986, Edited by Fred Brown: Cold Spring Harbor Laboratory.

Holmes, Eric H., "PSMA Specific antibodies and their diagnostic and therapeutic use," Exp. Opin. Invest. Drugs, 2001, 10(3), pp. 511-519.

Greenspan, Defining Epitopes: It's not as easy as it seems, Nature Biotechnology, vol. 17, Oct. 1999, pp. 936-937.

Alcantara-Neves, et al., "An Improved Method to Obtain Antigen-Excreting *Toxocara canis* Larvae," Experimental Parasitology, 2008, 119(3), pp. 349-351.

Watthanakulpanich, et al., "Application of *Toxocara canis* excretory—secretory antigens and IgG subclass antibodies (IgG1-4) in serodiagnostic assays of human toxocariasis," Acta Tropica, 2008, 106(2), pp. 90-95.

Iddawela, et al., "Characterization of a *Toxocara canis* Species-Specific Excretory-secretory antigen (TcES-57) and development of a double sandwich ELISA for diagnosis of visceral larva migrans," Korean Journal of Parasitology, 2007, 45(1), pp. 19-26.

Bethony, et al., "Antibodies against a secreted protein from hookworm larvae reduce the intensity of hookworm infection in humans and vaccinated laboratory animals", FASEB Journal, 2005, 19:1743-1745.

Croese, et al., "Occult enteric infection by *Ancylostoma caninum*: a previously unrecognized zoonosis", Gastroenterology, 1994, 106:3-12.

Gasser, et al. "Improved molecular diagnostic tools for human hookworms", Expert Rev. Mol. Diagn., 2009, 9(1): 17-21.

Johnson, et al., "Detection of gastrointestinal nematodes by a coproantigen capture ELISA", Res. Vet. Sci., 1996, 60:7-12.

Traub, et al., "Canine gastrointestinal parasitic zoonoses in India," Trends in Parasitology, 21(1): 42-48, 2005.

Bowie et al, "Deciphering the Message in Protein Sequences: Tolerance to Amino Acid Substitutions", Science, 1990, 247:1306-1310.

Uniprot submission P07852. Aug. 1, 1988. [Retrieved from the Internet Mar. 30, 2010: <URL:http://www.uniprot.org/uniprot/P07852>].

GenBank Accession No. AAD01628.1. Jan. 1999. [Retrieved from the Internet Feb. 25, 2010: <URL:http://ncbi.nlm.nih.gov/protein/410955)].

GenBank Accession No. BM965689.1. Mar. 2002. [Retrieved from the Internet Feb. 25, 2010: <URL:http://ncbi.nlm.nih.gov.nucest/19558140>).

GenBank Accession No. B0088667.1. Apr. 2002. [Retrieved from the Internet Feb. 25, 2010: <URL:http://ncbi.nlm.nih.gov.nucest/20062868>].

GenBank Accession No. AAC17174.1. May 1998. [Retrieved from the Internet Feb. 25, 2010: <URL:http://ncbi.nlm.nih.gov/protein/3152922>].

GenBank Accession No. AAC47345.1. Oct. 2007. [Retrieved from the Internet Feb. 25, 2010: <URL:http://ncbi.nlm.nih.gov/protein/1663728>].

GenBank Accession No. AAG31482.1. Nov. 2000. [Retrieved from the Internet Feb. 25, 2010: <URL:http://ncbi.nlm.nih.gov/protein/11138792>].

GenBank Accession No. NP_510821. Nov. 2008. [Retrieved from the Internet Feb. 25, 2010: <URL:http://ncbi.nlm.nih.gov/protein/17551598>].

Uniprot submission Q06811. Nov. 1997. [Retrieved from the Internet Feb. 25, 2010: <URL://www.uniprot.org/uniprot/Q06811>].

Uniprot submission Q24702. Nov. 1996. [Retrieved from the Internet Feb. 25, 2010: <URL:http://www/uniprot.org/uniprot/Q24702>].

Uniprot submission P91811. May 1997. [Retrieved from the Internet Feb. 25, 2010: <URL:http://uniprot.org/uniprot/P91811>].

Uniprot submission 044397. Jun. 1998. [Retrieved from the Internet Nov. 11, 2009: <URL:http://uniprot.org/uniprot/044397>].

Wakelin, "Acquired immunity to *Trichuris muris* in the albino laboratory mouse", Parasitology, 1967, 57:515-524.

Lillywhite et al., "Humoral immune responses in human infection with the whipworm *Trichuris trichiura*", Parasite Immunol., 1991, 13:491-507.

Drake et al., "The major secreted product of the whipworm, *Trichuris*, is a pore-forming protein", Proc. Biol. Sci., 1994, 257:255-261.

Jenkins et al., "Functional antigens of *Trichuris muris* released during in vitro maintenance: their immunogenicity and partial purification", Parasitology, 1983, 86:73-82.

Drake et al., "Molecular and functional characterization of a recombinant protein of *Trichuris trichiura*", Proc. Biol. Sci., 1998, 265:1559-1565.

Nukumi et al., "Whey acidic protein (WAP) regulates the proliferation of mammary epithelial cells by preventing serine protease from degrading laminin", J Cell Physiol., May 31, 2007, 213:793-800.

Barker et al., "Isolation of a gene family that encodes the porin-like proteins from the human parasitic nematode *Trichuris trichiura*", Gene, 1999, 229:131-136.

Parkinson et al., "400 000 nematode ESTs on the Net", Trends Parasitol., Jul. 2003, 19(7):283-286.

Lillywhite et al., "Identification and characterization of excreted/secreted products of *Trichuris trichiura*", Parasite Immunol., 1995, 17:47-54.

Daub et al., "A survey of genes expressed in adults of the human hookworm, *Necator americanus*", Parasitology, 2000, 120:171-184.

De Oliveira Vasconcelos, et al., "Identification of stage-specific proteins of *Angiostrongylus vasorum* (Baillet, 1866) Kamensky", Parasitol Res., 2007, 102(3):389-395.

Kania et al., "*Anoplocephala perfoliata* coproantigen detection: a preliminary study", Vet Parasitol, 2005, 127(2): 115-119.

Song et al., "Cross-reactivity between sera from dogs experimentally infected with *Dirofilaria immitis* and crude extract of *Toxocara canis*", Korean J Parasitol, Dec. 2002, 40(4):195-198.

Allan et al., "Coproantigen detection for immunodiagnosis of echinococcosis and taeniasis in dogs and humans", Parasitology, 1992, 104:347-355.

GenBank Accession No. CB098869. Jan. 28, 2003. [Retrieved from the Internet Mar. 30, 2010: <URL:http://ncbi.nlm.nih.gov/nucest/27924676>].

GenBank Accession No. CB099165. Jan. 28, 2003. [Retrieved from the Internet Mar. 30, 2010: <URL:http://ncbi.nlm.nih.gov/nucest/27924972>].

GenBank Accession No. CB099244. Jan. 28, 2003. [Retrieved from the Internet Mar. 30, 2010: <URL:http://ncbi.nlm.nih.gov/nucest/27925051>].

GenBank Accession No. CB099367. Jan. 28, 2003. [Retrieved from the Internet Mar. 30, 2010: <URL:http://ncbi.nlm.nih.gov/nucest/27925174>].

GenBank Accession No. CB188155. Feb. 5, 2003. [Retrieved from the Internet Mar. 30, 2010: <URL: http://ncbi.nlm.nih.gov/nucest/28251547>].

GenBank Accession No. CB188174. Feb. 5, 2003. [Retrieved from the Internet Mar. 30, 2010: <URL:http://ncbi.nlm.nih.gov/nucest/28251566>).

GenBank Accession No. CB188239. Feb. 5, 2003. [Retrieved from the Internet Mar. 30, 2010: <URL:http://ncbi.nlm.nih.gov/nucest/28251631>].

GenBank Accession No. CB188637. Feb. 5, 2003. [Retrieved from the Internet Mar. 30, 2010: <URL:http://ncbi. nlm.nih.gov/nucest/28252029>].

GenBank Accession No. CB189034. Feb. 5, 2003. [Retrieved from the Internet Mar. 30, 2010: <URL:http://ncbi.nlm.nih.gov/nucest/28252426>].

GenBank Accession No. CB189036. Feb. 5, 2003. [Retrieved from the Internet Mar. 30, 2010: <URL:http://ncbi.nlm.nih.gov/nucest/28252428>].

GenBank Accession No. CB189116. Feb. 5, 2003. [Retrieved from the Internet Mar. 30, 2010: <URL:http://ncbi.nlm.nih.gov/nucest/28252508>].

GenBank Accession No. CB189285. Feb. 5, 2003. [Retrieved from the Internet Mar. 30, 2010: <URL:http://ncbi.nlm.nih.gov/nucest/28252677>].

GenBank Accession No. CB189434. Feb. 5, 2003. [Retrieved from the Internet Mar. 30, 2010: <URL:http://ncbi.nlm.nih.gov/nucest/28252826>].

GenBank Accession No. CB277501. Feb. 25, 2003. [Retrieved from the Internet Mar. 30, 2010: <URL:http://ncbi.nlm.nih.gov/nucest/28561086>).

Gen Bank Accession No. CB277590. Feb. 25, 2003. [Retrieved from the Internet Mar. 30, 2010: <URL:http://ncbi.nlm.nih.gov/nucest/28561175>].

GenBank Accession No. CB277641. Feb. 25, 2003. [Retrieved from the Internet Mar. 30, 2010: <URL:http://ncbi.nlm.nih.gov/nucest/28561226>).

GenBank Accession No. CB277653. Feb. 25, 2003. [Retrieved from the Internet Mar. 30, 2010: <URL:http://ncbi.nlm.nih.gov/nucest/28561238>].

GenBank Accession No. CB277950. Feb. 25, 2003. [Retrieved from the Internet Mar. 30, 2010: <URL:http://ncbi.nlm.nih.gov/nucest/28561535>].

GenBank Accession No. CB188241. Feb. 5, 2003. [Retrieved from the Internet Mar. 30, 2010: <URL:http://ncbi.nlm.nih.gov/nucest/28251633>].

GenBank Accession No. CB277846. Feb. 25, 2003. [Retrieved from the Internet Mar. 30, 2010: <URL:http://ncbi.nlm.nih.gov/nucest/28561431>].

GenBank Accession No. CB277826. Feb. 25, 2003. [Retrieved from the Internet Mar. 30, 2010: <URL:http://ncbi.nlm.nih.gov/nucest/28561411>).

GenBank Accession No. CB189366. Feb. 5, 2003. [Retrieved from the Internet Mar. 30, 2010: <URL:http://ncbi.nlm.nih.gov/nucest/2852758>].

GenBank Accession No. CB098807. Jan. 28, 2003. [Retrieved from the Internet Mar. 30, 2010: <URL:http://ncbi.nlm.nih.gov/nucest/27924614>].

```
cattcactgc ggttgtaaaa gcagtgcaga aatgaggctg gtcttccatg cggttattta      60
cctcacattg gggttcctca ccgacgccgt aagagaaaaa cgtggcaaat gtcctcctga     120
accaccgatc gcaggaaaca cgatctactg ccgcgatgat tttgattgtg gaggaagaca     180
gaagtgctgt acaattgcag aaggacgtgg atgcgtgccg ccctatggtg aacaacattt     240
cgaagtggtg aaaccgggtc attgcccagc tattccagcg gttacgggca tggcgaactt     300
ctgtaacact gatggcgact gtgatggacc gaaaaaatgt tgtctcacat cgcgcggcta     360
cgattgcaca catccattac acttcccaat ccagccacaa cctccagtag gacagtgccc     420
tccttcaaag cccgtatcc caggaaaatg ggtagacatc tgcgctaagc atgccaactg     480
cccagaccca gagaagtgtt gcgacacgga gtatggcaac cgatgtatgg atgttggatt     540
agtgccagga caaggagaaa gaccagccaa ttgccgaac gaaccacgaa taagaggaac     600
taaatacgat tgccgacgag acgatgactg cgacggtgtg cagaaatgct gcttcactgt     660
tgagggacgt gagtgcgtgg aaccaagtag aaaaccactg gacaagcccg gacattgtcc     720
accaattccc gctgatgtgg gctcagccag gtactgcgac actgatcggg attgtgatgg     780
accaagaaaa tgctgcctct cttcgcgtgg ctatgaatgt aaacatccag tacactatcc     840
cgatcgagtg gagccactag taggagaatg cccaccatca cgacctcgca ttcctgggaa     900
atgggttgac atctgctcta agcatgccaa ctgcccagac ccagagaaat gttgcgacac     960
ggagtatggc aaccgatgta tggacgttgg attagtgcct ggacaaggag aaaacgctgc    1020
caactgccca aaggaaccac gaataagagg aactaagtac gactgtcgac gggacgatga    1080
ctgcgatgga aaacaaaagt gctgctacac aactgaaggc cgcgaatgcg tccatggtat    1140
atggccttaa atggttgctt cttcctataa taaaagcaaa cgaatcaaaa aaaaaaaaaa    1200
aaaaaaaaaa                                                          1210

(SEQ ID NO:1)
```

FIG. 1

```
gtaagagaaa aacgtggcaa atgtcctcct gaaccaccga tcgcaggaaa cacgatctac    60
tgccgcgatg attttgattg tggaggaaga cagaagtgct gtacaattgc agaaggacgt   120
ggatgcgtgc cgccctatgg tgaacaagat ttcgaagtgg tgaaaccggg tcattgccca   180
gctattccag cggttacggg catggcgaac ttctgtaaca ctgatggcga ctgtgatgga   240
ccgaaaaaat gttgtctcac atcgcgcgc tacgattgta cacatccgtt acacttccca   300
atccagccac aacctccagt aggacagtgc cctccttcaa agccccgtgt tccaggaaaa   360
tgggtagaca tctgcgctaa gcatgccaat tgcccagacc cagagaagtg ttgcgacacg   420
gagtatggca accgatgtat ggatgttgga ttagtggcag gacaaggaga aagaccaggc   480
aattgcccga acgaaccacg aataagagga actaaatacg attgccgacg agacgatgac   540
tgcgacggtg tgcagaaatg ctgcttcact gttgagggac gtgagtgcgt ggaaccaagc   600
agaaaaccac tggacaagcc cggacattgt ccaccaattc ccgctgatgt gggctcagcc   660
aggtactgcg acactgatcg ggattgtgat ggaccaagaa aatgctgcct ctcttcgcgt   720
ggctatgaat gtaaacatcc agtacactat cccgatcgag tggagccact agtaggagaa   780
tgcccaccat cacgacctcg cattcctggg aaatggttg acatctgctc taagcatgcc   840
aactgcccag acccagagaa atgttgcgac acggagtatg gcaaccgatg tatggacgtt   900
ggattagtgc ctggacaagg agaaaaacct gccaactgcc caaaggaacc acgaataagg   960
ggaactaagt acgactgtcg acgggacgat gactgcgatg ggaaacaaaa gtgctgctac  1020
acaactgaag gccgcgaatg cgtccatggt atatggcct                         1059
```

(SEQ ID NO:2)

FIG. 2

```
cattcactgc ggttgtaaaa gcagtgcaga aatgaggctg gtcttccatg cggttattta    60
                                         M  R  L  V  F  H  A  I  Y   10
cctcacattg gggttcctca ccgacgccgt aagagaaaaa cgtggcaaat gtcctcctga   120
 L  T  L  G  F  L  T  D  A  V  R  E  K  R  G  K  C  P  P  E         30
accaccgatc gcaggaaaca cgatctactg ccgcgatgat tttgattgtg gaggaagaca   180
 P  P  I  A  G  N  T  I  Y  C  R  D  D  F  D  C  G  R  Q           50
gaagtgctgt acaattgcag aaggacgtgg atgcgtgccg ccctatggtg aacaacattt   240
 K  C  C  T  I  A  E  G  R  G  C  V  P  P  Y  G  E  Q  H  F         70
cgaagtggtg aaaccgggtc attgcccagc tattccagcg gttacgggca tggcgaactt   300
 E  V  V  K  P  G  H  C  P  A  I  P  A  V  T  G  M  A  N  F         90
ctgtaacact gatggcgact gtgatggacc gaaaaaatgt tgtctcacat cgcgcggcta   360
 C  N  T  D  G  D  C  D  G  P  K  K  C  C  L  T  S  R  G  Y        110
cgattgcaca catccattac acttcccaat ccagccacaa cctccagtag gacagtgccc   420
 D  C  T  H  P  L  H  F  P  I  Q  P  Q  P  P  V  G  Q  C  P        130
tccttcaaag cccgtatcc caggaaaatg ggtagacatc tgcgctaagc atgccaactg   480
 P  S  K  P  R  I  P  G  K  W  V  D  I  C  A  K  H  A  N  C        150
cccagaccca gagaagtgtt gcgacacgga gtatggcaac cgatgtatgg atgttggatt   540
 P  D  P  E  K  C  C  D  T  E  Y  G  N  R  C  M  D  V  G  L        170
agtgccagga caaggagaaa gaccaggcaa ttgcccgaac gaaccacgaa taagaggaac   600
 V  P  G  Q  G  E  R  P  G  N  C  P  N  E  P  R  I  R  G  T        190
taaatacgat tgccgacgag acgatgactg cgacggtgtg cagaaatgct gcttcactgt   660
 K  Y  D  C  R  R  D  D  C  D  G  V  Q  K  C  C  F  T  V           210
tgagggacgt gagtgcgtga accaagtag aaaaccactg gacaagcccg gacattgtcc   720
 E  G  R  E  C  V  E  P  S  R  K  P  L  D  K  P  G  H  C  P        230
accaattccc gctgatgtgg gctcagccag gtactgcgac actgatcggg attgtgatgg   780
 P  I  P  A  D  V  G  S  A  R  Y  C  D  T  D  R  D  C  D  G        250
accaagaaaa tgctgcctct cttcgcgtgg ctatgaatgt aaacatccag tacactatcc   840
 P  R  K  C  C  L  S  R  G  Y  E  C  K  H  P  V  H  Y  P           270
cgatcgagtg gagccactag taggagaatg cccaccatca cgacctcgca ttcctgggaa   900
 D  R  V  E  P  L  V  G  E  C  P  P  S  R  P  I  P  G  K           290
atgggttgac atctgctcta agcatgccaa ctgcccagac ccagagaaat gttgcgacac   960
 W  V  D  I  C  S  K  H  A  N  C  P  D  P  E  K  C  C  D  T        310
ggagtatggc aaccgatgta tggacgttgg attagtgcct ggacaaggag aaaaacctgc  1020
 E  Y  G  N  R  C  M  D  V  G  L  V  P  G  Q  G  E  K  P  A        330
caactgccca aaggaaccac gaataagagg aactaagtac gactgtcgac gggacgatga  1080
 N  C  P  K  E  P  R  I  R  G  T  K  Y  D  C  R  R  D  D           350
ctgcgatggg aaacaaaagt gctgctacac aactgaaggc cgcgaatgcg tccatggtat  1140
 C  D  G  K  Q  K  C  C  Y  T  T  E  G  R  E  C  V  H  G  I        370
atggccttaa atggttgctt cttcctataa taaaagcaaa cgaatcaaaa aaaaaaaaa   1200
 W  P  *                                                            372
aaaaaaaaaa                                                          1210
```

(Nucleotide sequence is SEQ ID NO:1; Amino acid sequence is SEQ ID NO:3)

FIG. 3

```
gtaagagaaa aacgtggcaa atgtcctcct gaaccaccga tcgcaggaaa cacgatctac    60
 V  R  E  K  R  G  K  C  P  P  E  P  P  I  A  G  N  T  I  Y        20
tgccgcgatg attttgattg tggaggaaga cagaagtgct gtacaattgc agaaggacgt   120
 C  R  D  D  F  D  C  G  G  R  Q  K  C  C  T  I  A  E  G  R        40
ggatgcgtgc cgccctatgg tgaacaagat ttcgaagtgg tgaaaccggg tcattgccca   180
 G  C  V  P  P  Y  G  E  Q  D  F  E  V  V  K  P  G  H  C  P        60
gctattccag cggttacggg catggcgaac ttctgtaaca ctgatggcga ctgtgatgga   240
 A  I  P  A  V  T  G  M  A  N  F  C  N  T  D  G  D  C  D  G        80
ccgaaaaaat gttgtctcac atcgcgcggc tacgattgta cacatccgtt acacttccca   300
 P  K  K  C  C  L  T  S  R  G  Y  D  C  T  H  P  L  H  F  P       100
atccagccac aacctccagt aggacagtgc cctccttcaa agccccgtgt tccaggaaaa   360
 I  Q  P  Q  P  P  V  G  Q  C  P  P  S  K  P  R  V  P  G  K       120
tgggtagaca tctgcgctaa gcatgccaat tgcccagacc cagagaagtg ttgcgacacg   420
 W  V  D  I  C  A  K  H  A  N  C  P  D  P  E  K  C  C  D  T       140
gagtatggca accgatgtat ggatgttgga ttagtggcag gacaaggaga aagaccaggc   480
 E  Y  G  N  R  C  M  D  V  G  L  V  A  G  Q  G  E  R  P  G       160
aattgcccga acgaaccacg aataagagga actaaatacg attgccgacg agacgatgac   540
 N  C  P  N  E  P  R  I  R  G  T  K  Y  D  C  R  R  D  D  D       180
tgcgacggtg tgcagaaatg ctgcttcact gttgagggac gtgagtgcgt ggaaccaagc   600
 C  D  G  V  Q  K  C  F  T  V  E  G  R  E  C  V  E  P  S         200
agaaaaccac tggacaagcc cggacattgt ccaccaattc ccgctgatgt gggctcagcc   660
 R  K  P  L  D  K  P  G  H  C  P  P  I  P  A  D  V  G  S  A       220
aggtactgcg acactgatcg ggattgtgat ggaccaagaa aatgtcgcct ctcttcgcgt   720
 R  Y  C  D  T  D  R  D  C  D  G  P  R  K  C  C  L  S  S  R       240
ggctatgaat gtaaacatcc agtacactat cccgatcgag tggagccact agtaggagaa   780
 G  Y  E  C  K  H  P  V  H  Y  P  D  R  V  E  P  L  V  E         260
tgcccaccat cacgacctcg cattcctggg aaatgggttg acatctgctc taagcatgcc   840
 C  P  P  S  R  P  R  I  P  G  K  W  V  D  I  C  S  K  H  A       280
aactgcccag acccagagaa atgttgcgac acggagtatg gcaaccgatg tatggacgtt   900
 N  C  P  D  P  E  K  C  C  D  T  E  Y  G  N  R  C  M  D  V       300
ggattagtgc ctggacaagg agaaaaacct gccaactgcc caaaggaacc acgaataagg   960
 G  L  V  P  G  Q  G  E  K  P  A  N  C  P  K  E  P  R  I  R       320
ggaactaagt acgactgtcg acgggacgat gactgcgatg ggaaacaaaa gtgctgctac  1020
 G  T  K  Y  D  C  R  R  D  D  D  C  D  G  K  Q  K  C  C  Y       340
acaactgaag gccgcgaatg cgtccatggt atatggcct                         1059
 T  T  E  G  R  E  C  V  H  G  I  W  P                            353
```

(Nucleotide sequence is SEQ ID NO:2; Amino acid sequence is SEQ ID NO:4)

FIG. 4

```
Consensus (SEQ ID NO:9)  XXXXXXXXXXXXXXXXXXXXVREKRGKCPPEPPIAGNTIYCRDFFDCGGRQKCCTIAEGRGCVPPYGEQXFEVVKPGHCPA    80
                                 10        20        30        40        50        60        70        80
                        +---------+---------+---------+---------+---------+---------+---------+---------+
         (SEQ ID NO:3)  MRLVFHAVIYLTLGFLTDAVREKRGKCPPEPPIAGNTIYCRDFFDCGGRQKCCTIAEGRGCVPPYGEQHFEVVKPGHCPA    80
         (SEQ ID NO:4)  --------------------VREKRGKCPPEPPIAGNTIYCRDFFDCGGRQKCCTIAEGRGCVPPYGEQDFEVVKPGHCPA    61

Consensus (SEQ ID NO:9)  IPAVTGMANFCNTDGDCDGPRKCCLTSRGYDCTHPLRFPIQPQPPVGQCPPSKPRXPGKWVDICAKHANCPDPEKCCDTE   160
                                 90       100       110       120       130       140       150       160
                        +---------+---------+---------+---------+---------+---------+---------+---------+
         (SEQ ID NO:3)  IPAVTGMANFCNTDGDCDGPRKCCLTSRGYDCTHPLRFPIQPQPPVGQCPPSKPRIPGKWVDICAKHANCPDPEKCCDTE   160
         (SEQ ID NO:4)  IPAVTGMANFCNTDGDCDGPRKCCLTSRGYDCTHPLRFPIQPQPPVGQCPPSKPRVPGKWVDICAKHANCPDPEKCCDTE   141

Consensus (SEQ ID NO:9)  YGNRCMDVGLVXGQGERPGMCFNEPRIRGTKYDCRRDDDCDGVQKCCFTVEGRECVEPSRKFLDKPGHCPFIPADVGSAR   240
                                170       180       190       200       210       220       230       240
                        +---------+---------+---------+---------+---------+---------+---------+---------+
         (SEQ ID NO:3)  YGNRCMDVGLVPGQGERPGMCFNEPRIRGTKYDCRRDDDCDGVQKCCFTVEGRECVEPSRKFLDKPGHCPFIPADVGSAR   240
         (SEQ ID NO:4)  YGNRCMDVGLVAGQGERPGMCFNEPRIRGTKYDCRRDDDCDGVQKCCFTVEGRECVEPSRKFLDKPGHCPFIPADVGSAR   221

Consensus (SEQ ID NO:9)  YCDTDRDCDGPRKCCLSSRGYECKHPVHYPDRVEPLVGECPPSRPRIPGKWVDICSKHANCPDPEKCCDTEYGNRCMDVG   320
                                250       260       270       280       290       300       310       320
                        +---------+---------+---------+---------+---------+---------+---------+---------+
         (SEQ ID NO:3)  YCDTDRDCDGPRKCCLSSRGYECKHPVHYPDRVEPLVGECPPSRPRIPGKWVDICSKHANCPDPEKCCDTEYGNRCMDVG   320
         (SEQ ID NO:4)  YCDTDRDCDGPRKCCLSSRGYECKHPVHYPDRVEPLVGECPPSRPRIPGKWVDICSKHANCPDPEKCCDTEYGNRCMDVG   301

Consensus (SEQ ID NO:9)  LVPGQGEKPANCPKEPRIRGTKYDCRRDDDCDGKQKCCYTTEGRECVHGIWP   372
                                330       340       350       360       370
                        +---------+---------+---------+---------+---------+
         (SEQ ID NO:3)  LVPGGQEKPANCPKEPRIRGTKYDCRRDDDCDGKQKCCYTTEGRECVHGIWP   372
         (SEQ ID NO:4)  LVPGGQEKPANCPKEPRIRGTKYDCRRDDDCDGKQKCCYTTEGRECVHGIWP   353
```

FIG. 5

SEQUENCE LISTING

<160> NUMBER OF SEQ ID NOS: 9

<210> SEQ ID NO 1
<211> LENGTH: 1210
<212> TYPE: DNA
<213> ORGANISM: Trichuris vulpis

<400> SEQUENCE: 1

```
cattcactgc ggttgtaaaa gcagtgcaga aatgaggctg gtcttccatg cggttattta      60
cctcacattg gggttcctca ccgacgccgt aagagaaaaa cgtggcaaat gtcctcctga     120
accaccgatc gcaggaaaca cgatctactg ccgcgatgat tttgattgtg gaggaagaca     180
```

-continued

| | |
|---|---|
| gaagtgctgt acaattgcag aaggacgtgg atgcgtgccg ccctatggtg aacaacattt | 240 |
| cgaagtggtg aaaccgggtc attgcccagc tattccagcg gttacgggca tggcgaactt | 300 |
| ctgtaacact gatggcgact gtgatggacc gaaaaaatgt tgtctcacat cgcgcggcta | 360 |
| cgattgcaca catccattac acttcccaat ccagccacaa cctccagtag acagtgccc | 420 |
| tccttcaaag ccccgtatcc caggaaaatg gtagacatc tgcgctaagc atgccaactg | 480 |
| cccagaccca gagaagtgtt gcgacacgga gtatggcaac cgatgtatgg atgttggatt | 540 |
| agtgccagga caaggagaaa gaccaggcaa ttgcccgaac gaaccacgaa taagaggaac | 600 |
| taaatacgat tgccgacgag acgatgactg cgacggtgtg cagaaatgct gcttcactgt | 660 |
| tgagggacgt gagtgcgtgg aaccaagtag aaaaccactg acaagcccg acattgtcc | 720 |
| accaattccc gctgatgtgg gctcagccag gtactgcgac actgatcggg attgtgatgg | 780 |
| accaagaaaa tgctgcctct cttcgcgtgg ctatgaatgt aaacatccag tacactatcc | 840 |
| cgatcgagtg gagccactag taggagaatg cccaccatca cgacctcgca ttcctgggaa | 900 |
| atgggttgac atctgctcta agcatgccaa ctgcccagac cagagaaat gttgcgacac | 960 |
| ggagtatggc aaccgatgta tggacgttgg attagtgcct ggacaaggag aaaaacctgc | 1020 |
| caactgccca aggaaccac gaataagagg aactaagtac gactgtcgac gggacgatga | 1080 |
| ctgcgatggg aaacaaaagt gctgctacac aactgaaggc cgcgaatgcg tccatggtat | 1140 |
| atggccttaa atggttgctt cttcctataa taaaagcaaa cgaatcaaaa aaaaaaaaaa | 1200 |
| aaaaaaaaaa | 1210 |

<210> SEQ ID NO 2
<211> LENGTH: 1059
<212> TYPE: DNA
<213> ORGANISM: Trichuris vulpis

<400> SEQUENCE: 2

| | |
|---|---|
| gtaagagaaa aacgtggcaa atgtcctcct gaaccaccga tcgcaggaaa cacgatctac | 60 |
| tgccgcgatg attttgattg tggaggaaga cagaagtgct gtacaattgc agaaggacgt | 120 |
| ggatgcgtgc cgcccctatgg tgaacaagat ttcgaagtgg tgaaaccggg tcattgccca | 180 |
| gctattccag cggttacggg catggcgaac ttctgtaaca ctgatggcga ctgtgatgga | 240 |
| ccgaaaaaat gttgtctcac atcgcgcggc tacgattgta cacatccgtt acacttccca | 300 |
| atccagccac aacctccagt aggacagtgc cctccttcaa agccccgtgt tccaggaaaa | 360 |
| tgggtagaca tctgcgctaa gcatgccaat tgcccagacc cagagaagtg ttgcgacacg | 420 |
| gagtatggca accgatgtat ggatgttgga ttagtggcag acaaggagaa agaccaggc | 480 |
| aattgcccga cgaaccacg aataagagga actaaatacg attgccgacg agacgatgac | 540 |
| tgcgacggtg tgcagaaatg ctgcttcact gttgagggac gtgagtgcgt ggaaccaagc | 600 |
| agaaaaccac tggacaagcc cggacattgt ccaccaattc ccgctgatgt gggctcagcc | 660 |
| aggtactgcg acactgatcg ggattgtgat ggaccaagaa aatgctgcct ctcttcgcgt | 720 |
| ggctatgaat gtaaacatcc agtacactat cccgatcgag tggagccact agtaggagaa | 780 |
| tgcccaccat cacgacctcg cattcctggg aaatggggttg acatctgctc taagcatgcc | 840 |
| aactgcccag acccagagaa atgttgcgac acggagtatg caaccgatg tatggacgtt | 900 |
| ggattagtgc ctggacaagg agaaaaacct gccaactgcc caaggaacc acgaataagg | 960 |
| ggaactaagt acgactgtcg acgggacgat gactgcgatg ggaaacaaaa gtgctgctac | 1020 |
| acaactgaag gccgcgaatg cgtccatggt atatggcct | 1059 |

-continued

<210> SEQ ID NO 3
<211> LENGTH: 372
<212> TYPE: PRT
<213> ORGANISM: Trichuris vulpis

<400> SEQUENCE: 3

```
Met Arg Leu Val Phe His Ala Val Ile Tyr Leu Thr Leu Gly Phe Leu
1               5                   10                  15

Thr Asp Ala Val Arg Glu Lys Arg Gly Lys Cys Pro Pro Glu Pro Pro
            20                  25                  30

Ile Ala Gly Asn Thr Ile Tyr Cys Arg Asp Asp Phe Asp Cys Gly Gly
        35                  40                  45

Arg Gln Lys Cys Cys Thr Ile Ala Glu Gly Arg Gly Cys Val Pro Pro
    50                  55                  60

Tyr Gly Glu Gln His Phe Glu Val Val Lys Pro Gly His Cys Pro Ala
65                  70                  75                  80

Ile Pro Ala Val Thr Gly Met Ala Asn Phe Cys Asn Thr Asp Gly Asp
                85                  90                  95

Cys Asp Gly Pro Lys Lys Cys Cys Leu Thr Ser Arg Gly Tyr Asp Cys
            100                 105                 110

Thr His Pro Leu His Phe Pro Ile Gln Pro Gln Pro Pro Val Gly Gln
        115                 120                 125

Cys Pro Pro Ser Lys Pro Arg Ile Pro Gly Lys Trp Val Asp Ile Cys
    130                 135                 140

Ala Lys His Ala Asn Cys Pro Asp Pro Glu Lys Cys Cys Asp Thr Glu
145                 150                 155                 160

Tyr Gly Asn Arg Cys Met Asp Val Gly Leu Val Pro Gly Gln Gly Glu
                165                 170                 175

Arg Pro Gly Asn Cys Pro Asn Glu Pro Arg Ile Arg Gly Thr Lys Tyr
            180                 185                 190

Asp Cys Arg Arg Asp Asp Asp Cys Asp Gly Val Gln Lys Cys Cys Phe
        195                 200                 205

Thr Val Glu Gly Arg Glu Cys Val Glu Pro Ser Arg Lys Pro Leu Asp
    210                 215                 220

Lys Pro Gly His Cys Pro Pro Ile Pro Ala Asp Val Gly Ser Ala Arg
225                 230                 235                 240

Tyr Cys Asp Thr Asp Arg Asp Cys Asp Gly Pro Arg Lys Cys Cys Leu
                245                 250                 255

Ser Ser Arg Gly Tyr Glu Cys Lys His Pro Val His Tyr Pro Asp Arg
            260                 265                 270

Val Glu Pro Leu Val Gly Glu Cys Pro Pro Ser Arg Pro Arg Ile Pro
        275                 280                 285

Gly Lys Trp Val Asp Ile Cys Ser Lys His Ala Asn Cys Pro Asp Pro
    290                 295                 300

Glu Lys Cys Cys Asp Thr Glu Tyr Gly Asn Arg Cys Met Asp Val Gly
305                 310                 315                 320

Leu Val Pro Gly Gln Gly Glu Lys Pro Ala Asn Cys Pro Lys Glu Pro
                325                 330                 335

Arg Ile Arg Gly Thr Lys Tyr Asp Cys Arg Arg Asp Asp Asp Cys Asp
            340                 345                 350

Gly Lys Gln Lys Cys Cys Tyr Thr Thr Glu Gly Arg Glu Cys Val His
        355                 360                 365

Gly Ile Trp Pro
    370
```

<210> SEQ ID NO 4
<211> LENGTH: 353
<212> TYPE: PRT
<213> ORGANISM: Trichuris vulpis

<400> SEQUENCE

```
<210> SEQ ID NO 5
<211> LENGTH: 354
<212> TYPE: PRT
<213> ORGANISM: Artificial
<220> FEATURE:
<223> OTHER INFORMATION: Synthetic

<400> SEQUENCE: 5

Met Val Arg Glu Lys Arg Gly Lys Cys Pro Pro Glu Pro Pro Ile Ala
1               5                   10                  15

Gly Asn Thr Ile Tyr Cys Arg Asp Asp Phe Asp Cys Gly Gly Arg Gln
            20                  25                  30

Lys Cys Cys Thr Ile Ala Glu Gly Arg Gly Cys Val Pro Pro Tyr Gly
        35                  40                  45

Glu Gln His Phe Glu Val Val Lys Pro Gly His Cys Pro Ala Ile Pro
    50                  55                  60

Ala Val Thr Gly Met Ala Asn Phe Cys Asn Thr Asp Gly Asp Cys Asp
65                  70                  75                  80

Gly Pro Lys Lys Cys Cys Leu Thr Ser Arg Gly Tyr Asp Cys Thr His
                85                  90                  95

Pro Leu His Phe Pro Ile Gln Pro Gln Pro Val Gly Gln Cys Pro
            100                 105                 110

Pro Ser Lys Pro Arg Ile Pro Gly Lys Trp Val Asp Ile Cys Ala Lys
            115                 120                 125

His Ala Asn Cys Pro Asp Pro Glu Lys Cys Cys Asp Thr Glu Tyr Gly
            130                 135                 140

Asn Arg Cys Met Asp Val Gly Leu Val Pro Gly Gln Gly Glu Arg Pro
145                 150                 155                 160

Gly Asn Cys Pro Asn Glu Pro Arg Ile Arg Gly Thr Lys Tyr Asp Cys
                165                 170                 175

Arg Arg Asp Asp Asp Cys Asp Gly Val Gln Lys Cys Cys Phe Thr Val
            180                 185                 190

Glu Gly Arg Glu Cys Val Glu Pro Ser Arg Lys Pro Leu Asp Lys Pro
            195                 200                 205

Gly His Cys Pro Pro Ile Pro Ala Asp Val Gly Ser Ala Arg Tyr Cys
            210                 215                 220

Asp Thr Asp Arg Asp Cys Asp Gly Pro Arg Lys Cys Cys Leu Ser Ser
225                 230                 235                 240

Arg Gly Tyr Glu Cys Lys His Pro Val His Tyr Pro Asp Arg Val Glu
                245                 250                 255

Pro Leu Val Gly Glu Cys Pro Pro Ser Arg Pro Arg Ile Pro Gly Lys
            260                 265                 270

Trp Val Asp Ile Cys Ser Lys His Ala Asn Cys Pro Asp Pro Glu Lys
            275                 280                 285

Cys Cys Asp Thr Glu Tyr Gly Asn Arg Cys Met Asp Val Gly Leu Val
290                 295                 300

Pro Gly Gln Gly Glu Lys Pro Ala Asn Cys Pro Lys Glu Pro Arg Ile
305                 310                 315                 320

Arg Gly Thr Lys Tyr Asp Cys Arg Arg Asp Asp Cys Asp Gly Lys
                325                 330                 335

Gln Lys Cys Cys Tyr Thr Thr Glu Gly Arg Glu Cys Val His Gly Ile
            340                 345                 350

Trp Pro
```

```
<210> SEQ ID NO 6
<211> LENGTH: 353
<212> TYPE: PRT
<213> ORGANISM: Artificial
<220> FEATURE:
<223> OTHER INFORMATION: Synthetic

<400> SEQUENCE: 6

Val Arg Glu Lys Arg Gly Lys Cys Pro Pro Glu Pro Ile Ala Gly
1               5                   10                  15

Asn Thr Ile Tyr Cys Arg Asp Asp Phe Asp Cys Gly Gly Arg Gln Lys
                20                  25                  30

Cys Cys Thr Ile Ala Glu Gly Arg Gly Cys Val Pro Pro Tyr Gly Glu
            35                  40                  45

Gln His Phe Glu Val Val Lys Pro Gly His Cys Pro Ala Ile Pro Ala
        50                  55                  60

Val Thr Gly Met Ala Asn Phe Cys Asn Thr Asp Gly Asp Cys Asp Gly
65                  70                  75                  80

Pro Lys Lys Cys Cys Leu Thr Ser Arg Gly Tyr Asp Cys Thr His Pro
                85                  90                  95

Leu His Phe Pro Ile Gln Pro Gln Pro Val Gly Cys Pro Pro
                100                 105                 110

Ser Lys Pro Arg Ile Pro Gly Lys Trp Val Asp Ile Cys Ala Lys His
            115                 120                 125

Ala Asn Cys Pro Asp Pro Glu Lys Cys Cys Asp Thr Glu Tyr Gly Asn
        130                 135                 140

Arg Cys Met Asp Val Gly Leu Val Pro Gly Gln Gly Glu Arg Pro Gly
145                 150                 155                 160

Asn Cys Pro Asn Glu Pro Arg Ile Arg Gly Thr Lys Tyr Asp Cys Arg
                165                 170                 175

Arg Asp Asp Asp Cys Asp Gly Val Gln Lys Cys Cys Phe Thr Val Glu
            180                 185                 190

Gly Arg Glu Cys Val Glu Pro Ser Arg Lys Pro Leu Asp Lys Pro Gly
        195                 200                 205

His Cys Pro Pro Ile Pro Ala Asp Val Gly Ser Ala Arg Tyr Cys Asp
            210                 215                 220

Thr Asp Arg Asp Cys Asp Gly Pro Arg Lys Cys Cys Leu Ser Ser Arg
225                 230                 235                 240

Gly Tyr Glu Cys Lys His Pro Val His Tyr Pro Asp Arg Val Glu Pro
                245                 250                 255

Leu Val Gly Glu Cys Pro Pro Ser Arg Pro Arg Ile Pro Gly Lys Trp
            260                 265                 270

Val Asp Ile Cys Ser Lys His Ala Asn Cys Pro Asp Pro Glu Lys Cys
        275                 280                 285

Cys Asp Thr Glu Tyr Gly Asn Arg Cys Met Asp Val Gly Leu Val Pro
290                 295                 300

Gly Gln Gly Glu Lys Pro Ala Asn Cys Pro Lys Glu Pro Arg Ile Arg
305                 310                 315                 320

Gly Thr Lys Tyr Asp Cys Arg Arg Asp Asp Cys Asp Gly Lys Gln
                325                 330                 335

Lys Cys Cys Tyr Thr Thr Glu Gly Arg Glu Cys Val His Gly Ile Trp
            340                 345                 350

Pro
```

```
<210> SEQ ID NO 7
<211> LENGTH: 354
<212> TYPE: PRT
<213> ORGANISM: Artificial
<220> FEATURE:
<223> OTHER INFORMATION: Synthetic

<400> SEQUENCE: 7

Met Val Arg Glu Lys Arg Gly Lys Cys Pro Pro Glu Pro Pro Ile Ala
1               5                   10                  15

Gly Asn Thr Ile Tyr Cys Arg Asp Asp Phe Asp Cys Gly Gly Arg Gln
            20                  25                  30

Lys Cys Cys Thr Ile Ala Glu Gly Arg Gly Cys Val Pro Pro Tyr Gly
        35                  40                  45

Glu Gln Asp Phe Glu Val Val Lys Pro Gly His Cys Pro Ala Ile Pro
    50                  55                  60

Ala Val Thr Gly Met Ala Asn Phe Cys Asn Thr Asp Gly Asp Cys Asp
65                  70                  75                  80

Gly Pro Lys Lys Cys Cys Leu Thr Ser Arg Gly Tyr Asp Cys Thr His
                85                  90                  95

Pro Leu His Phe Pro Ile Gln Pro Gln Pro Val Gln Cys Pro
            100                 105                 110

Pro Ser Lys Pro Arg Val Pro Gly Lys Trp Val Asp Ile Cys Ala Lys
            115                 120                 125

His Ala Asn Cys Pro Asp Pro Glu Lys Cys Cys Asp Thr Glu Tyr Gly
130                 135                 140

Asn Arg Cys Met Asp Val Gly Leu Val Ala Gly Gln Gly Glu Arg Pro
145                 150                 155                 160

Gly Asn Cys Pro Asn Glu Pro Arg Ile Arg Gly Thr Lys Tyr Asp Cys
                165                 170                 175

Arg Arg Asp Asp Asp Cys Asp Gly Val Gln Lys Cys Cys Phe Thr Val
            180                 185                 190

Glu Gly Arg Glu Cys Val Glu Pro Ser Arg Lys Pro Leu Asp Lys Pro
        195                 200                 205

Gly His Cys Pro Pro Ile Pro Ala Asp Val Gly Ser Ala Arg Tyr Cys
    210                 215                 220

Asp Thr Asp Arg Asp Cys Asp Gly Pro Arg Lys Cys Cys Leu Ser Ser
225                 230                 235                 240

Arg Gly Tyr Glu Cys Lys His Pro Val His Tyr Pro Asp Arg Val Glu
                245                 250                 255

Pro Leu Val Gly Glu Cys Pro Pro Ser Arg Pro Arg Ile Pro Gly Lys
            260                 265                 270

Trp Val Asp Ile Cys Ser Lys His Ala Asn Cys Pro Asp Pro Glu Lys
        275                 280                 285

Cys Cys Asp Thr Glu Tyr Gly Asn Arg Cys Met Asp Val Gly Leu Val
    290                 295                 300

Pro Gly Gln Gly Glu Lys Pro Ala Asn Cys Pro Lys Glu Pro Arg Ile
305                 310                 315                 320

Arg Gly Thr Lys Tyr Asp Cys Arg Arg Asp Asp Cys Asp Gly Lys
                325                 330                 335

Gln Lys Cys Cys Tyr Thr Thr Glu Gly Arg Glu Cys Val His Gly Ile
            340                 345                 350

Trp Pro
```

<210> SEQ ID NO 8
<211> LENGTH: 353
<212> TYPE: PRT
<213> ORGANISM: Artificial
<220> FEATURE:
<223> OTHER INFORMATION: Synthetic

<400> SEQUENCE: 8

```
Val Arg Glu Lys Arg Gly Lys Cys Pro Pro Glu Pro Ile Ala Gly
1               5                   10                  15

Asn Thr Ile Tyr Cys Arg Asp Asp Phe Asp Cys Gly Gly Arg Gln Lys
            20                  25                  30

Cys Cys Thr Ile Ala Glu Gly Arg Gly Cys Val Pro Pro Tyr Gly Glu
        35                  40                  45

Gln Asp Phe Glu Val Val Lys Pro Gly His Cys Pro Ala Ile Pro Ala
    50                  55                  60

Val Thr Gly Met Ala Asn Phe Cys Asn Thr Asp Gly Asp Cys Asp Gly
65                  70                  75                  80

Pro Lys Lys Cys Cys Leu Thr Ser Arg Gly Tyr Asp Cys Thr His Pro
                85                  90                  95

Leu His Phe Pro Ile Gln Pro Gln Pro Val Gly Gln Cys Pro Pro
            100                 105                 110

Ser Lys Pro Arg Val Pro Gly Lys Trp Val Asp Ile Cys Ala Lys His
        115                 120                 125

Ala Asn Cys Pro Asp Pro Glu Lys Cys Cys Asp Thr Glu Tyr Gly Asn
    130                 135                 140

Arg Cys Met Asp Val Gly Leu Val Ala Gly Gln Gly Glu Arg Pro Gly
145                 150                 155                 160

Asn Cys Pro Asn Glu Pro Arg Ile Arg Gly Thr Lys Tyr Asp Cys Arg
                165                 170                 175

Arg Asp Asp Asp Cys Asp Gly Val Gln Lys Cys Cys Phe Thr Val Glu
            180                 185                 190

Gly Arg Glu Cys Val Glu Pro Ser Arg Lys Pro Leu Asp Lys Pro Gly
        195                 200                 205

His Cys Pro Pro Ile Pro Ala Asp Val Gly Ser Ala Arg Tyr Cys Asp
    210                 215                 220

Thr Asp Arg Asp Cys Asp Gly Pro Arg Lys Cys Cys Leu Ser Ser Arg
225                 230                 235                 240

Gly Tyr Glu Cys Lys His Pro Val His Tyr Pro Asp Arg Val Glu Pro
                245                 250                 255

Leu Val Gly Glu Cys Pro Pro Ser Arg Pro Arg Ile Pro Gly Lys Trp
            260                 265                 270

Val Asp Ile Cys Ser Lys His Ala Asn Cys Pro Asp Pro Glu Lys Cys
        275                 280                 285

Cys Asp Thr Glu Tyr Gly Asn Arg Cys Met Asp Val Gly Leu Val Pro
    290                 295                 300

Gly Gln Gly Glu Lys Pro Ala Asn Cys Pro Lys Glu Pro Arg Ile Arg
305                 310                 315                 320

Gly Thr Lys Tyr Asp Cys Arg Arg Asp Asp Cys Asp Gly Lys Gln
                325                 330                 335

Lys Cys Cys Tyr Thr Thr Glu Gly Arg Glu Cys Val His Gly Ile Trp
            340                 345                 350

Pro
```

-continued

```
<210> SEQ ID NO 9
<211> LENGTH: 372
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (1)..(19)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (136)..(136)
<223> OTHER INFORMATION: Xaa can be any naturally occurring amino acid
<220> FEATURE:
<221> NAME/KEY: misc_feature
<222> LOCATION: (172)..(172)
<223> OTHER INFORMATION: Xaa can be any naturally occurring amino acid

<400> SEQUENCE: 9

Xaa Xaa Xaa Xaa Xaa Xaa Xaa Xaa Xaa Xaa Xaa Xaa Xaa Xaa Xaa
 1               5                  10                  15

Xaa Xaa Xaa Val Arg Glu Lys Arg Gly Lys Cys Pro Pro Glu Pro Pro
                20                  25                  30

Ile Ala Gly Asn Thr Ile Tyr Cys Arg Asp Asp Phe Asp Cys Gly Gly
             35                  40                  45

Arg Gln Lys Cys Cys Thr Ile Ala Glu Gly Arg Gly Cys Val Pro Pro
         50                  55                  60

Tyr Gly Glu Gln Xaa Phe Glu Val Val Lys Pro Gly His Cys Pro Ala
 65                  70                  75                  80

Ile Pro Ala Val Thr Gly Met Ala Asn Phe Cys Asn Thr Asp Gly Asp
                 85                  90                  95

Cys Asp Gly Pro Lys Lys Cys Cys Leu Thr Ser Arg Gly Tyr Asp Cys
            100                 105                 110

Thr His Pro Leu His Phe Pro Ile Gln Pro Gln Pro Pro Val Gly Gln
        115                 120                 125

Cys Pro Pro Ser Lys Pro Arg Xaa Pro Gly Lys Trp Val Asp Ile Cys
130                 135                 140

Ala Lys His Ala Asn Cys Pro Asp Pro Glu Lys Cys Cys Asp Thr Glu
145                 150                 155                 160

Tyr Gly Asn Arg Cys Met Asp Val Gly Leu Val Xaa Gly Gln Gly Glu
                165                 170                 175

Arg Pro Gly Asn Cys Pro Asn Glu Pro Arg Ile Arg Gly Thr Lys Tyr
            180                 185                 190

Asp Cys Arg Arg Asp Asp Asp Cys Asp Gly Val Gln Lys Cys Cys Phe
        195                 200                 205

Thr Val Glu Gly Arg Glu Cys Val Glu Pro Ser Arg Lys Pro Leu Asp
    210                 215                 220

Lys Pro Gly His Cys Pro Pro Ile Pro Ala Asp Val Gly Ser Ala Arg
225                 230                 235                 240

Tyr Cys Asp Thr Asp Arg Asp Cys Asp Gly Pro Arg Lys Cys Cys Leu
                245                 250                 255

Ser Ser Arg Gly Tyr Glu Cys Lys His Pro Val His Tyr Pro Asp Arg
            260                 265                 270

Val Glu Pro Leu Val Gly Glu Cys Pro Pro Ser Arg Pro Arg Ile Pro
        275                 280                 285
```

-continued

```
Gly Lys Trp Val Asp Ile Cys Ser Lys His Ala Asn Cys Pro Asp Pro
    290                 295             300

Glu Lys Cys Cys Asp Thr Glu Tyr Gly Asn Arg Cys Met Asp Val Gly
305             310             315                         320

Leu Val Pro Gly Gln Gly Glu Lys Pro Ala Asn Cys Pro Lys Glu Pro
            325                 330                 335

Arg Ile Arg Gly Thr Lys Tyr Asp Cys Arg Arg Asp Asp Asp Cys Asp
            340             345             350

Gly Lys Gln Lys Cys Cys Tyr Thr Thr Glu Gly Arg Glu Cys Val His
        355             360                 365

Gly Ile Trp Pro
    370
```

METHODS, DEVICES, KITS AND COMPOSITIONS FOR DETECTING WHIPWORM

CROSS REFERENCE

This application is a divisional of U.S. Ser. No. 12/467,794, filed May 18, 2009 (now U.S. Pat. No. 7,993,861) which in turn claims the benefit of priority to U.S. Provisional Patent Application Ser. No. 61/128,077, filed May 19, 2008, which is incorporated by reference herein in its entirety.

BACKGROUND OF THE INVENTION

1. Field of the Invention

The present invention relates to compositions, devices, kits and methods for the detection of whipworm in mammals. More particularly, the present invention relates to polypeptides and polypeptide compositions, antibodies and antibody compositions, devices, kits, and methods for detecting the presence or absence of whipworm antigen in a sample from a mammal that may also include one or more of hookworm, roundworm, and heartworm antigen.

2. Description of the Prior Art

Adult whipworms live in the intestine and lay eggs that pass out in the feces. In the environment, eggs embryonate in as little as one to three weeks (but eggs may survive in soil for as long as five years before hatching). Embryonated eggs enter a host by ingestion. Larvae then hatch in the small intestine before penetrating the wall of the cecum, where they remain for up to 10 days. After hatching, larvae migrate to the large intestine, where they develop into adult worms.

Intestinal whipworm infection is common in animals and, if left untreated, can cause serious disease and even death. Although it is relatively easy to determine that an animal harbors a parasitic worm (helminth) infection of some type, it is significantly more difficult to identify whipworm, specifically, as the causative worm, primarily due to intermittent shedding of eggs into the environment. This is a problem because whipworm infections are best treated when the infected animal's caregiver has knowledge that whipworm is the specific source of the infection.

Current methods for diagnosis of whipworm infections primarily involve microscopic examination of fecal samples, either directly in fecal smears or following concentration of ova by flotation in density media. Despite this procedure's high adoption, the method has significant shortcomings. These microscopic methods are time consuming, are unpleasant, require specialized equipment and have low specificity and sensitivity (Dryden et al., 2005 Vet. Therap. 6(1), 15). In addition, the accuracy of results of these methods is highly dependent upon the skill and expertise of the operator.

Stool handling is disagreeable and hazardous. Sanitary and inoffensive procedures for processing stool are awkward and often complex. Such procedures may include weighing, centrifuging and storing, and are difficult except in a clinical laboratory equipped with a suitable apparatus, protective equipment, and a skilled technician. Therefore, any reduction in the number of steps required to perform a fecal test and any reduction in contact between test operator and the test material is desirable. Clinical laboratories have been using the immunoassay methods for the detection of various viruses, bacteria and non-helminth parasites and organisms in feces. However, there remains a need for a simple immunoassay method for the detection of a parasitic worm infection, and whipworm infection in particular in feces, whole blood or in serum.

SUMMARY OF THE INVENTION

In one aspect, the invention includes antibodies that specifically bind to a polypeptide including all or an antigenic portion of the amino acid sequence that corresponds to one or more of SEQ ID NO:3 through SEQ ID NO:9, as listed herein, or to a polypeptide including a sequence that is a conservative variant of one of those sequences. In a further aspect, the antibodies specifically bind to antigen from whipworm-infested mammals, but do not specifically bind antigen from mammals infected with hookworm, roundworm and/or heartworm.

In another aspect, the invention includes antibodies that are obtained by immunization with the polypeptide including all or an antigenic portion of the amino acid sequence that corresponds to one or more of SEQ ID NO:3 through SEQ ID NO:9, or with a polypeptide including a sequence that is a conservative variant of one of those sequences.

In yet another aspect, the invention provides a device for detecting the presence or absence of whipworm antigens from a sample; the device comprising a solid support, wherein the solid support has immobilized thereon one or more antibodies that are capable of specifically binding to a polypeptide that has an amino acid sequence that corresponds to SEQ ID NO:3, SEQ ID NO:4, SEQ ID NO:5, SEQ ID NO:6, SEQ ID NO:7, SEQ ID NO:8, or SEQ ID NO: 9, or an antigenic portion thereof. The device, may be, but is not limited to being, for example, an ELISA device, such as a lateral flow immunoassay device or microtiterplate device. Mammalian samples that may be tested for whipworm by the device include, but are not limited to being, feces and whole tissue, such as tissue from small intestine, large intestine, cecum, colon, rectum, or other tissue obtained from the gastrointestinal tract, for example. The device further may include, but need not include, one or more reagents for the detection of one or more of the group consisting of: one or more non-whipworm worm parasites, one or more non-worm parasites, one or more viruses, one or more fungi, and one or more bacteria.

In yet another aspect, the invention provides a method of detecting the presence or absence of whipworm, such as *Trichuris vulpis, Trichuris campanula, Trichuris serrata, Trichuris suis, Trichuris trichiura, Trichuris discolor* and *Trichocephalus trichiuris*, for example, in a sample. The sample can be obtained from a mammal, such as a canine, feline, porcine, bovine, or human. In one aspect, the method is carried out to test a fecal sample for whipworm coproantigen. The method, however, is not limited to being carried out to test a fecal sample. In addition to feces, the sample therefore may be, but is not limited to being whole tissue, such as tissue from small intestine, large intestine, cecum, colon, rectum, or other tissue obtained from the gastrointestinal tract, for example. Steps of the method include contacting the sample with one or more of the antibodies of the invention; forming antibody polypeptide complexes in the presence of the polypeptides if any, in the sample; and detecting the presence or absence of the antibody-polypeptide complexes, if any. The method further may include one or more of the optional steps of diagnosing the mammal as either having or not having a whipworm infection and determining whether a nucleic acid from whipworm is present in the same sample that was contacted with the antibodies for the purpose of detecting the presence or absence of whipworm or in some other sample from the mammal. The method may also be used to test for environmental contamination with whipworm. Environmental samples that may be tested for whipworm by the device include, but are not limited to soil, decomposing material, or fecal matter from residential settings including yards, gardens, sand boxes, playgrounds. Testing locations may also include parks, beaches, forests, farms, or other locations exposed to fecal material from dogs, cats, or other mammalian hosts of whipworms. Feces from indoor and outdoor litter boxes may also be tested.

In yet another aspect, the present invention includes a kit for carrying out one or more steps of the method of the invention. The kit may optionally include, for example, the device and one or more of the compositions of the present invention and instructions for carrying out the method of the present invention. The kit may further optionally include, for example, one or more indicator reagents, one or more antibody labeling compounds, one or more antibodies, one or more antigen capture reagents, one or more inhibitors, and one or more wash reagents to be used as part of the device and/or to be used in carrying out the method.

BRIEF DESCRIPTION OF THE DRAWINGS

FIG. 1 shows the nucleotide sequence of a 1210-nucleotide cDNA sequence from whole adult *Trichuris vulpis* (SEQ ID NO:1).

FIG. 2 shows the nucleotide sequence of a 1059-nucleotide cDNA sequence from whole adult *Trichuris vulpis*. (SEQ ID NO:2).

FIG. 3 shows the amino acid sequence (SEQ ID NO:3) of a large open reading frame (ORF) of SEQ ID NO:1. The stop codon is indicated by *.

FIG. 4 shows the amino acid sequence (SEQ ID NO:4) of a large ORF of SEQ ID NO:2. The stop codon is indicated by *.

FIG. 5 shows a comparison alignment of SEQ ID NO:3 and SEQ ID NO:4. The consensus sequence of SEQ ID NO:3 and SEQ ID NO:4 is shown as SEQ ID NO:9.

DETAILED DESCRIPTION OF THE PREFERRED EMBODIMENTS OF THE INVENTION

Introduction

Figure 6A:
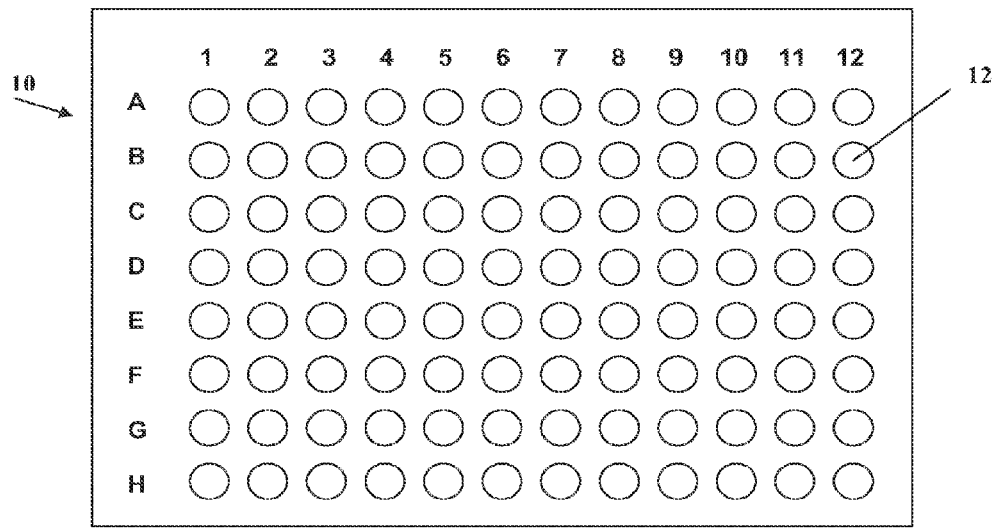
FIG. 6A shows a multi-well plate device of the present invention.

The present invention is generally directed to methods, devices, kits and compositions for detecting whipworm in a fecal sample obtained from a mammal. The present invention relates to whipworm coproantigens from *Trichuris*, such as *Trichuris vulpis*, for example. In particular, the present invention relates to *Trichuris* polypeptides and conservative variants thereof, polynucleotides that encode those polypeptides and oligonucleotides that specifically bind to those polynucleotides, antibodies that are raised against and that specifically bind those polypeptides, and methods, devices and kits for detecting whipworm, such as *Trichuris vulpis*, for example.

The present invention provides a superior alternative to these existing microscopic inspection techniques. This is true because the present invention provides compositions, devices, kits and methods for detecting the presence or absence of whipworm in a sample from a mammal that: (1) are both easy to use and yield consistently reliable results; (2) allow for the absence or presence of whipworm in a mammal to be confirmed regardless of whether that mammal is infected with hookworm, roundworm, and/or heartworm; and (3) can detect whipworm prior to the time that whipworm ova first appear in the infected host's feces.

The present invention is based in part on the discovery of unexpected properties of compositions of the present invention. Specifically, it was determined that an antibody of the present invention raised against a polypeptide of the present invention can be used to capture and detect whipworm antigens in a mammal, even when the mammal is also infested by one or more of hookworm, roundworm and heartworm. This specificity for whipworm is surprising because whipworms, roundworms, hookworms and heartworms all are related nematodes, and an antibody raised against a protein isolated from any one of these worms would be expected to crossreact with one or more of the other worms, host antigens, or other host components.

It was further determined that this antibody can be used to capture and detect whipworm antigens in a mammal as early as 31 days after the mammal is first infected with whipworm. This ability to detect whipworm so soon after infection, and before the appearance of any whipworm ova in the feces of the infected mammal, is surprising because whipworm ova generally do not appear in the feces of an infective host until about 10 weeks after the host becomes infected.

The present invention therefore includes methods, devices, compositions and kits that use antibodies and/or fragments thereof to specifically capture and detect whipworm antigens in a mammal that may also be infested by one or more of roundworm, hookworm and heartworm. The ability of the present invention to detect and diagnose whipworm even when one or more other worm types are also present allows the mammal's caregiver the opportunity to optimally select a treatment for ridding the whipworm from the mammal. Further, the ability of the present invention to, in some cases, detect whipworm as early as 31 days after the mammal is first infected provides the possibility that the caregiver may begin such treatment before the mammal becomes severely sickened by the whipworm. An intervention prior to appearance of ova in the feces would also greatly reduce or eliminate the possibility that the infestation is spread to other animals or humans.

DEFINITIONS AND USES OF TERMS

The term "compositions of the invention" refers to all of the nucleic acids, polypeptides, antibodies, and mixtures that include one or more of those nucleic acids, polypeptides, and antibodies and one or more other compounds, that can be used to detect the presence or absence of whipworm in a sample obtained from a mammal by carrying out the method of the present invention that are explicitly described, implicitly encompassed or otherwise disclosed herein.

"A sample from a mammal" in which whipworm can be detected by the present invention includes all bodily components and extracts thereof, such as any fluid, solid, cell or tissue, that are capable of containing whipworm antigen. Exemplary samples therefore include, but are not limited to being, feces and whole tissue, such as tissue from small intestine, large intestine, cecum, colon, rectum, or other tissue obtained from the gastrointestinal tract, for example. The sample may be taken directly from the mammal or the sample may be taken from anything that has contacted the mammal. For example, the sample may be fresh or decaying fecal droppings from the mammal. As another example, the sample may include soil, dirt, sand, plant material, or any other material that may be mixed with bodily components that may be left behind by a mammal, such as feces, for example. No matter the origin or the content of the sample, this sample sometimes is referred to herein as the "mammalian sample", the "test sample" or the "sample under test".

As used herein, "nucleic acid" is synonymous with, and therefore is used interchangeably with, "gene", "DNA", "cDNA", "EST", "polynucleotide", "oligonucleotide", "polynucleic acid", "RNA" and "mRNA". A nucleic acid may be in double-stranded form or it may be in single-stranded form. Further, a nucleic acid is either naturally isolated, such as from a whole whipworm or a portion thereof, for example, or it is artificially synthesized, either in a recombinant host organism or by any other artificial means known to the skilled artisan, such as by employing a PCR-based technique, by creating a transgenic organism that synthesizes the nucleic acid, by using a DNA synthesizing machine, or by any another molecular-based technique, for example.

"Polypeptide", "peptide" and "protein" are synonymous terms that are used interchangeably herein to refer to a polymer of amino acid residues. A polypeptide, peptide and protein of the present invention may be either naturally isolated, such as from a whole whipworm or from a portion of whipworm, for example, or artificially synthesized, either in a recombinant host organism or by any other artificial means known to the skilled artisan.

The term "antibody" or "antibody of the present invention" refers to any antibody that is able to specifically bind to one or more whipworm antigens, but not to any antigen from hookworm, roundworm or heartworm. The antibodies of the present invention may be raised against one or more immunogenic polypeptides of the present invention. Unless otherwise stated, it is to be understood that the antibody of the present invention may include a mixture of two or more different types of antibody. For example, the antibody may be a mixture of two types of antibodies, wherein one of the two types specifically binds to one particular antigen and the other of the two types specifically binds to some other antigen.

The "immunogenic polypeptide of the present invention" and, more simply, "the polypeptide of the present invention", is an immunogen against which the antibodies of the present invention may be raised. All "polypeptides of the present invention" are immunogenic and therefore may be used to elicit an immune response in a host animal to produce the antibodies of the present invention. Unless otherwise stated, it is to be understood that the polypeptide of the present invention may be one component of a mixed composition of a plurality of components.

An "immunogen" is any agent, such as the immunogenic polypeptide of the present invention, for example, that is capable of eliciting an immune response in an animal that is exposed to that agent.

The term "whipworm", as used herein, refers to helminths such as intestinal whipworms of the order *Trichurida*. Exemplary whipworms therefore include *Trichuris vulpis, Trichuris campanula, Trichuris serrata, Trichuris suis, Trichuris trichiura, Trichuris discolor* and *Trichocephalus trichiuris*. Further, the term "whipworm", as used herein, does not refer to the entirety of the phylum Nematoda. For example, "whipworm" does not include any member of the genera *Ancylostoma, Uncinaria, Necator, Toxocara, Toxascaris, Ascaris* or *Dirofilaria*.

A "whipworm coproantigen" or a "coproantigen of whipworm" is any whipworm product that is present in the feces of a mammal having a whipworm infection and that may be specifically bound by one or more of the antibodies of the invention. For example, a whipworm coproantigen may be, but is not limited to being, one or more of the polypeptides of the invention.

"Specific for", "specifically binds", and "stably binds" means that a particular composition of the invention, such as an antibody, polypeptide, or oligonucleotide of the present invention, for example, recognizes and binds to one or more other agents with greater affinity than to at least one other agent. As one example, an antibody of the present invention is said to be "specific for", to "specifically bind", and to "stably bind" whipworm antigens whenever that antibody is able to recognize and bind to those whipworm antigens with greater affinity than to any other antigens from a non-whipworm parasitic worm. Such binding specificity can be tested using methodology well known in the art, for example, ELISA or a radioimmunoassay (RIA). Based on information observed regarding the binding specificity of a particular composition of the invention, the method of the present invention can be carried out under conditions that allow that composition to bind to (and therefore to allow the detection of such binding to) a particular agent or agents, but not to significantly bind other agents, while those conditions are maintained. As one example, the method of the present invention can be carried out under conditions that allow an antibody of the present invention to bind to (and therefore to allow the detection of such binding to) one or more whipworm antigens present in a particular sample, but not significantly to any hookworm, roundworm or heartworm antigen that may be present in that sample.

"Detecting whipworm" means detecting one or more whipworm-specific products, including one or more of the polypeptides, antibodies and nucleic acids of the present invention, or one or more whipworm antigens, for example. The presence of one or more such whipworm products in a sample from a mammal is indicative that the mammal has a whipworm infection, regardless of whether any whole whipworm organism or ovum thereof is also present in that sample. Conversely, the absence of one or more such whipworm products a sample from a mammal is indicative that the mammal does not have a whipworm infection.

"Amino acid" refers to naturally occurring and synthetic amino acids. Amino acid residues are abbreviated as follows: Alanine is A or Ala; Arginine is R or Arg; Asparagine is N or Asn; Aspartic Acid is D or Asp; Cysteine is C or Cys; Glutamic Acid is E or Glu; Glutamine is Q or Gln; Glycine is G or Gly; Histidine is H or His; Isoleucine is I or Ile; Leucine is L or Leu; Lysine is K or Lys; Methionine is M or Met; Phenylalanine is F or Phe; Proline is P or Pro; Serine is S or Ser; Threonine is T or Thr; Tryptophan is W or Trp; Tyrosine is Y or Tyr; and Valine is V or Val. Except where defined otherwise herein, X or Xaa represents any amino acid. Other relevant amino acids include, but are not limited to being, 4-hydroxyproline and 5-hydroxylysine. In all cases, the amino acid sequence of a polypeptide described or otherwise referred to herein is presented in conventional form in that the left-most, or first, amino acid residue of the sequence is the N-terminal residue and the right-most, or last, amino acid residue of the sequence is the C-terminal residue.

A "conservative variant" of any particular nucleic acid sequence includes any sequence having one or more degenerate codon substitutions to that particular nucleic acid sequence, any sequence having one or more nucleotide substitutions to, insertions to, and deletions from that particular nucleic acid sequence, and the complementary sequence of that particular nucleic acid and the conservative variants of that complementary sequence. Conservative variants of a particular nucleic acid sequence preferably have at least about 85% identity, more preferably have at least about 90% identity, and even more preferably at least about 95-99% identity, to that particular nucleic acid sequence. Conservative variants of a particular nucleic acid sequence may be artificially synthesized or they may be isolated in their natural form from an organism, including from a whipworm organism, such as *Trichuris* and *Trichocephalus*, for example.

A "conservative variant" of any particular polypeptide sequence is any polypeptide having an amino acid sequence that varies from the amino acid sequence of that particular polypeptide but still retains the specific binding properties of that particular polypeptide, such that an antibody of the present invention that is raised against the particular polypeptide is capable of specifically binding the variant polypeptide. Therefore, for example, a conservative variant of a particular polypeptide may have one or more amino acid substitutions, deletions, additions, and insertions to that particular polypeptide. For example, a conserved variant of a particular polypeptide may have 30 or fewer, 25 or fewer, 20 or fewer, 15 or fewer, 10 or fewer, or 5 or fewer, conserved amino acid substitutions to that particular polypeptide. Conservative variants of a particular polypeptide preferably, but not essentially, have at least about 80% identity, more preferably have at least about 90% identity, and even more preferably at least about 91-99% identity, to that particular polypeptide. A percent identity for any subject nucleic acid or amino acid sequence (e.g., any of polypeptides described herein) relative to another "target" nucleic acid or amino acid sequence can be determined as follows. First, a target nucleic acid or amino acid sequence of the invention can be compared and aligned to a subject nucleic acid or amino acid sequence, using the BLAST 2 Sequences (B12seq) program from the stand-alone version of BLASTZ containing BLASTN and BLASTP (e.g., version 2.0.14). The stand-alone version of BLASTZ can be obtained at www.ncbi.nlm.nih.gov. Instructions explaining how to use BLASTZ, and specifically the B12seq program, can be found in the 'readme' file accompanying BLASTZ. The programs also are described in detail by Karlin et al. (1990) Proc. Natl. Acad. Sci. 87:2264; Karlin et al. (1990) Proc. Natl. Acad. Sci. 90:5873; and Altschul et al. (1997) Nucl. Acids Res. 25:3389.

B12seq performs a comparison between the subject sequence and a target sequence using either the BLASTN (used to compare nucleic acid sequences) or BLASTP (used to compare amino acid sequences) algorithm. Typically, the default parameters of a BLOSUM62 scoring matrix, gap existence cost of 11 and extension cost of 1, a word size of 3, an expect value of 10, a per residue cost of 1 and a lambda ratio of 0.85 are used when performing amino acid sequence alignments. The output file contains aligned regions, of homology between the target sequence and the subject sequence. Once aligned, a length is determined by counting the number of consecutive nucleotides or amino acid residues (i.e., excluding gaps) from the target sequence that align with sequence from the subject sequence starting with any matched position and ending with any other matched position. A matched position is any position where an identical nucleotide or amino acid residue is present in both the target and subject sequence. Gaps of one or more residues can be inserted into a target or subject sequence to maximize sequence alignments between structurally conserved domains (e.g., $\alpha$-helices, $\beta$-sheets, and loops).

The percent identity over a particular length is determined by counting the number of matched positions over that particular length, dividing that number by the length and multiplying the resulting value by 100. For example, if (i) a 500 amino acid target sequence is compared to a subject amino acid sequence, (ii) the B12seq program presents 200 amino acids from the target sequence aligned with a region of the subject sequence where the first and last amino acids of that 200 amino acid region are matches, and (iii) the number of matches over those 200 aligned amino acids is 180, then the 500 amino acid target sequence contains a length of 200 and a sequence identity over that length of 90% (i.e., 180/200× 100=90). It will be appreciated that a nucleic acid or amino acid target sequence that aligns with a subject sequence can result in many different lengths with each length having its own percent identity. It is noted that the percent identity value can be rounded to the nearest tenth. For example, 78.11, 78.12, 78.13, and 78.14 is rounded down to 78.1, while 78.15, 78.16, 78.17, 78.18, and 78.19 is rounded up to 78.2. It is also noted that the length value will always be an integer.

Conservative variants of a particular polypeptide sequence may be artificially synthesized or they may be isolated in their natural form from an organism, including from a whipworm organism, such as *Trichuris* and *Trichocephalus*, for example. In one specific example, the polypeptide of the invention having an amino acid sequence corresponding to SEQ ID NO:4 shown below is a conservative variant of the polypeptide of the present invention having an amino acid sequence corresponding to SEQ ID NO:6 in that SEQ ID NO:4 is more than 99% identical to SEQ ID NO:6 over an alignment of 353 amino acids. More generally, each one of SEQ ID NO:3 through SEQ ID NO:9 are conserved variants of each other. It is also to be understood that other conserved variants of the SEQ ID NO:3 through SEQ ID NO:9 are contemplated by the present invention as described herein, but the skilled artisan would recognize that all of these contemplated variants are too numerous to list. The skilled artisan will also recognize that these variants include, but are not limited to, those have one or more substitutions of basic amino acid residues, one or more substitutions of acidic amino acid residues, one or more substitutions of polar amino acid residues, one or more substitutions of hydrophobic amino acid residues, one or more substitutions of aromatic amino acid residues, and one or more substitutions of small amino acid residues. ("Basic" amino acid residues are K, R and H. "Acidic" amino acid residues are D and E. "Polar" amino acid residues are N and Q. "Hydrophobic" amino acids are I, L, and V. "Aromatic" amino acid residues are F, Y, and W. "Small" amino acids are G, S, A, T and M.)

Nucleic Acids and Polypeptides of the Invention

The nucleic acids and polypeptides of the invention are described in detail in Provisional Application: "Methods, Devices, Kits And Compositions For Detecting Whipworm," Application Ser. No. 61/128,077, filed May 19, 2008, which is incorporated by reference in its entirety.

In an attempt to identify compositions that may be used to confirm the presence or absence of whipworm in a fecal sample, a plurality of oligonucleotide primers were designed, synthesized and used in 5' RACE, 3'RACE and RT-PCR reactions that included total RNA isolated from whole adult *Trichuris vulpis*. As a result of these efforts, a 1210-nucleotide cDNA sequence and a 1059-nucleotide cDNA sequence were deduced (these sequence is shown in FIGS. 1 and 2 and are identified herein as SEQ ID NO:1 and SEQ ID NO:2, respectively. BLAST searches that were carried out using SEQ ID NO:1 and SEQ ID NO:2 indicated these sequences are likely to encode a porin, which is a whipworm excretory/secretory protein that is similar to a protein that has been described in the mouse parasite *Trichuris muris* and the human parasite *Trichuris trichiuria*.

Analysis of the sequences corresponding to SEQ ID NO:1 and SEQ ID NO:2 indicated that each one of these sequences contains a large ORF. Specifically, as shown in FIG. 3, the large ORF of SEQ ID NO:1 corresponds to nucleotides 32 through 1147 of SEQ ID NO:1 and is predicted to encode a polypeptide having the following amino acid sequence:

(SEQID NO: 3)
MRLVFHAVIYLTLGFLTDAVREKRGKCPPEPPIAGNTIYCRDDFDCGG

RQKCCTIAEGRGCVPPYGEQHFEVVKPGHCPAIPAVTGMANFCNTDGDR

CDGPKKCCLTSGYDCTHPLHFPIQPQPPVGQCPPSKPRIPGKWVDICAK

HANCPDPEKCCDTEYGNRCMDVGLVPGQGERPGNCPNEPRIRGTKYDCR

RDDDCDGVQKCCFTVEGRECVEPSRKPLDKPGHCPPIPADVGSARYCDT

DRDCDGPRKCCLSSRGYECKHPVHYPDRVEPLVGECPPSRPRIPGKWVD

ICSKHANCPDPEKCCDTEYGNRCMDVGLVPGQGEKPANCPKEPRIRGTK

YDCRRDDDCDGKQKCCYTTEGRECVHGIWP.

Further, as shown in FIG. 4, the large ORF of SEQ ID NO:2 corresponds to nucleotides 1 through 1059 of SEQ ID NO:2 and is predicted to encode a polypeptide having the following amino acid sequence:

(SEQ ID NO: 4)
VREKRGKCPPEPPIAGNTIYCRDDFDCGGRQKCCTIAEGRGCVPPYGE

QDFEVVKPGHCPAIPAVTGMANFCNTDGDCDGPKKCCLTSRGYDCTHP

LHFPIQPQPPVGQCPPSKPRVPGKWVDICAKHANCPDPEKCCDTEYGN

RCMDVGLVAGQGERPGNCPNEPRIRGTKYDCRRDDDCDGVQKCCFTVE

GRECVEPSRKPLDKPGHCPPIPADVGSARYCDTDRDCDGPRKCCLSSR

GYECKHPVHYPDRVEPLVGECPPSRPRIPGKWVDICSKHANCPDPEKC

CDTEYGNRCMDVGLVPGQGEKPANCPKEPRIRGTKYDCRRDDDCDGKQ

KCCYTTEGRECVHGIWP.

The polypeptides of the present invention may be encoded for by nucleic acids that have a nucleotide sequence that corresponds to all or portions of SEQ ID NO:1 and SEQ ID NO:2 or to all or portions of any conservative variant of those sequences. It is to be understood therefore that the amino acid sequence of the polypeptide of the present invention is variable.

For example, the polypeptide of the present invention may have an amino acid sequence that corresponds to all or a portion of SEQ ID NO:3 or SEQ ID NO:4 or all or a portion of any conservative variant of SEQ ID NO:3 or SEQ ID NO:4.

In one specific example, the polypeptide of the present invention has the following amino acid sequence:

(SEQ ID NO: 5)
MVREKRGKCPPEPPIAGNTIYCRDDFDCGGRQKCCTIAEGRGCVPPY

GEQHFEVVKPGHCPAIPAVTGMANFCNTDGDCDGPKKCCLTSRGYDC

THPLHFPIQPQPPVGQCPPSKPRIPGKWVDICAKHANCPDPEKCCDT

EYGNRCMDVGLVPGQGERPGNCPNEPRIRGTKYDCRRDDDCDGVQKC

CFTVEGRECVEPSRKPLDKPGHCPPIPADVGSARYCDTDRDCDGPRK

CCLSSRGYECKHPVHYPDRVEPLVGECPPSRPRIPGKWVDICSKHANC

PDPEKCCDTEYGNRCMDVGLVPGQGEKPANCPKEPRIRGTKYDCRRD

DDCDGKQKCCYTTEGRECVHGIWP.

The 353 amino acid residues that follow the N-terminal methionine residue of the polypeptide corresponding to SEQ ID NO:5 specifically represent the amino acid residues 20 through 353 of SEQ ID NO:3. As described in the Example section included herein, the N-terminal methionine was artificially added to the N-terminus of this polypeptide by carrying out a standard cloning technique. Also as described throughout the Example section, antibody raised against the polypeptide corresponding to SEQ ID NO:5 was useful for detecting whipworm antigen. Because the N-terminal methionine was artificially added, and is not thought to naturally exist in *Trichuris vulpis* (the residue that is immediately prior to the valine residue at position 20 in SEQ ID NO:3 is alanine), it is therefore contemplated that the polypeptide of the present invention may have an amino acid sequence that corresponds to amino acid residues 20 through 353 of SEQ ID NO:3, or, more specifically:

(SEQ ID NO: 6)
VREKRGKCPPEPPIAGNTIYCRDDFDCGGRQKCCTIAEGRGCVPPY

GEQHFEVVKPGHCPAIPAVTGMANFCNTDGDCDGPKKCCLTSRGYD

CTHPLHFPIQPQPPVGQCPPSKPRIPGKWVDICAKHANCPDPEKCC

DTEYGNRCMDVGLVPGQGERPGNCPNEPRIRGTKYDCRRDDDCDGV

QKCCFTVEGRECVEPSRKPLDKPGHCPPIPADVGSARYCDTDRDCD

GPRKCCLSSRGYECKHPVHYPDRVEPLVGECPPSRPRIPGKWVDIC

SKHANCPDPEKCCDTEYGNRCMDVGLVPGQGEKPANCPKEPRIRGT

KYDCRRDDDCDGKQKCCYTTEGRECVHGIWP.

In another specific example, the polypeptide of the present invention has the following amino acid sequence:

(SEQ ID NO: 7)
MVREKRGKCPPEPPIAGNTIYCRDDFDCGGRQKCCTIAEGRGCVPPY

GEQDFEVVKPGHCPAIPAVTGMANFCNTDGDCDGPKKCCLTSRGYDC

THPLHFPIQPQPPVGQCPPSKPRVPGKWVDICAKHANCPDPEKCCDT

EYGNRCMDVGLVAGQGERPGNCPNEPRIRGTKYDCRRDDDCDGVQKC

CFTVEGRECVEPSRKPLDKPGHCPPIPADVGSARYCDTDRDCDGPRK

CCLSSRGYECKHPVHYPDRVEPLVGECPPSRPRIPGKWVDICSKHA

NCPDPEKCCDTEYGNRCMDVGLVPGQGEKPANCPKEPRIRGTKYDCR

RDDDCDGKQKCCYTTEGRECVHGIWP.

The 353 amino acid residues that follow the N-terminal methionine residue of the polypeptide corresponding to SEQ ID NO:7 specifically represent the amino acid residues 1 through 353 of SEQ ID NO:4. As described in the Example section included herein, the N-terminal methionine was artificially added to the N-terminus of this polypeptide by carrying out a standard cloning technique. Also as described throughout the Example section, antibody raised against the polypeptide corresponding to SEQ ID NO:7 was useful for detecting whipworm antigen. Because the N-terminal methionine was artificially added, it is therefore contemplated that the polypeptide of the present invention may have an amino acid sequence that corresponds to amino acid residues 1 through 353 of SEQ ID NO:4, or, more specifically:

(SEQ ID NO: 8)
VREKRGKCPPEPPIAGNTIYCRDDFDCGGRQKCCTIAEGRGCVPPYG

EQDFEVVKPGHCPAIPAVTGMANFCNTDGDCDGPKKCCLTSRGYDC

THPLHFPIQPQPPVGQCPPSKPRVPGKWVDICAKHANCPDPEKCCDT

EYGNRCMDVGLVAGQGERPGNCPNEPRIRGTKYDCRRDDDCDGVQKC

CFTVEGRECVEPSRKPLDKPGHCPPIPADVGSARYCDTDRDCDGPRK

CCLSSRGYECKHPVHYPDRVEPLVGECPPSRPRIPGKWVDICSKHAN

CPDPEKCCDTEYGNRCMDVGLVPGQGEKPANCPKEPRIRGTKYDCRR

DDDCDGKQKCCYTTEGRECVHGIWP.

Further, an alignment of SEQ ID NO:3 with respect to SEQ ID NO:4 is shown in FIG. 5. It is additionally contemplated that the polypeptide of the present invention may have the amino acid sequence corresponding to SEQ ID NO:9 (which also is shown in FIG. 5), wherein the X at position 1 is M or absent, the X at position 2 is R or absent, the X at position 3 is L or absent, the X at position 4 is V or absent, the X at position 5 is F or absent, the X at position 6 is H or absent, the X at position 7 is A or absent, the X at position 8 is V or absent, the X at position 9 is I or absent, the X at position 10 is Y or absent, the X at position 11 is L or absent, the X at position 12 is T or absent, the X at position 13 is L or absent, the X at position 14 is G or absent, the X at position 15 is F or absent, the X at position 16 is L or absent, the X at position 17 is T or absent, the X at position 18 is D or absent, the X at position 19 is A or is absent (or the X at position 19 is M, which occupies position 19 of SEQ ID NO:5), the X at position 69 is H or D, the X at position 136 is I or V and the X at position 172 is P or A.

It is also contemplated that any one or more of the SEQ ID NO:3 through SEQ ID NO:9 may be only a portion of a larger polypeptide sequence, and therefore may represent partial sequence of one or more proteins that normally are expressed in whipworm, for example, or one or more polypeptide sequences that are artificially fused to SEQ ID NO:3 through SEQ ID NO:9. The skilled artisan will recognize that are a variety of techniques exist for artificially fusing two or more polypeptide fragments together.

It is even further contemplated that the polypeptide of the present invention may include more than one of the SEQ ID NO:3 through SEQ ID NO:9. For example, the polypeptide of the present invention may include the SEQ ID NO:5 fused to the SEQ ID NO:7. Also, it is contemplated that the polypeptide of the present invention may include a plurality of polypeptide fragments corresponding to SEQ ID NO:3 through SEQ ID NO:9. For example, the polypeptide of the present invention may be formed by a plurality of polypeptide fragments corresponding to SEQ ID NO:5 that are fused together. In another example, the polypeptide of the present invention may be formed by a plurality of polypeptide fragments corresponding to SEQ ID NO:5 and a plurality of polypeptide fragments corresponding to SEQ ID NO:7 that are fused together in any combination.

Whereas one particular polypeptide of the present invention was expressed and isolated by a specific technique (in which is described in the Example section included herein), the skilled artisan will recognize that any of the polypeptides of the present invention may be isolated by employing any one or more of a variety of techniques. (See, e.g., Sewald and Jakubke, *Peptides: Chemistry and Biology*, Wiley Publishing (2002); *Peptide Synthesis and Applications (Methods in Molecular Biology)* Howl, ed., Humana Press (2005); Jones, *Amino Acid and Peptide Synthesis*, Oxford University Press (2002), each one of which is incorporated herein by reference in its entirety.) These techniques include those that may be carried out to isolate naturally existing polypeptides having amino acid sequence corresponding to SEQ ID NO:3 through SEQ ID NO:9 and any naturally occurring variant of those polypeptides. These techniques further include those that may be carried out to artificially generate the polypeptides having amino acid sequence corresponding to SEQ ID NO:3 through SEQ ID NO:9 and any conserved variant of those polypeptides. Such variants may be generated, for example, by employing any one or more mutagenesis techniques or by direct synthesis.

The polypeptides of the present invention are capable of eliciting an immune response in a host animal that is exposed to these polypeptides to produce one or more of the antibodies of the present invention. Regardless of the technique by which they are derived, the polypeptides of the present invention are preferably prepared in substantially pure form when they are to be used for the purpose of raising antibody. Preferably, these polypeptides are at least about 80% pure, more preferably are at least about 90-95% pure, and even more preferably are at least about 99% pure. Exemplary techniques for eliciting an immune response in a host organism and for isolating antibodies therefrom are described herein, but it is to be understood that the present invention is not limited to those techniques. The skilled artisan will recognize that there are a plurality of techniques for achieving this same goal without deviating from the scope and spirit of the invention.

Antibodies of the Invention

The present invention further includes antibodies and antigen-binding fragments thereof that are raised against and that specifically bind all or part of one or more polypeptides of the present invention, and also includes compositions that include said antibodies and antigen-binding fragments thereof. When contacted to a sample obtained from a mammal, these antibodies and antigen-binding fragments are able to specifically bind whipworm antigen present in the sample, but are not able to specifically bind any antigen from hookworm, roundworm, or heartworm that may be present in the sample. The antibodies of the present invention are suitable for being used only to capture one or more whipworm antigens, only to detect one or more whipworm antigens, or more preferably, to both capture and detect one or more whipworm antigens.

The antibodies of the present invention may belong to any antibody class, including for example, IgG, IgM, IgA, IgD and IgE, and may be prepared by any of a variety of techniques known to the skilled artisan. (See, e.g., Dean, *Methods Mol. Biol.* 80:23-37 (1998); Dean, *Methods Mol. Biol.* 32:361-79 (1994); Baileg, *Methods Mol. Biol.* 32:381-88 (1994); Gullick, *Methods Mol. Biol.* 32:389-99 (1994); Drenckhahn et al. *Methods Cell. Biol.* 37:7-56 (1993); Morrison, *Ann. Rev. Immunol.* 10:239-65 (1992); Wright et al. *Crit. Rev. Immunol.* 12:125-68 (1992); Harlow and Lane, *Antibodies: A Laboratory Manual*, Cold Spring Harbor Laboratory (1988); and *Making and Using Antibodies: A Practical Handbook*, Howard and Kaser, eds., CRC Press (2006), each one of which is incorporated herein by reference in its entirety.)

In one technique, the polypeptide of the invention is introduced into a host animal, such as into rabbit, mouse, rat, guinea pig, goat, pig, cow, sheep, donkey, dog, cat, chicken, or horse, for example. An enhanced immune response may be elicited in the host animal by associating the polypeptide with a carrier and/or by exposing the host to an adjuvant, but it is to be understood that the present invention does not require that the polypeptide be associated with a carrier or that the host be exposed to the adjuvant. An exemplary carrier that may be used for this purpose is bovine serum albumin, bovine thyroglobulin, and soybean trypsin inhibitor. Exemplary adjuvants include Freund's complete or incomplete adjuvant and MDL-TDM adjuvant. Regardless of whether the polypeptide is associated with such a carrier or whether the host is exposed to an adjuvant, booster immunizations optionally may be made with the host animal being bled one or more times thereafter. Polyclonal antibodies that specifically bind the polypeptide may then be purified from antisera obtained from the bleed or bleeds. Such purification may be achieved, for example, by employing affinity chromatography techniques that involve associating the polypeptide to a solid support. Such affinity chromatography techniques are well known by the skilled artisan.

In one embodiment, the antibody of the present invention is an antibody that is raised in rabbit by immunizing that host animal with the polypeptide having the amino acid sequence corresponding to SEQ ID NO:5. (Hereinafter, this particular antibody is referred to as "anti-DIV6901".) A specific technique for producing and isolating anti-DIV6901 pAB is described in the Example section included herein, but the skilled artisan will recognize that the production and isolating of anti-DIV6901 pAB, or any other antibody of the present invention, is not limited to that specific technique.

In another embodiment, the antibody of the present invention is an antibody that is raised in rabbit by immunizing that host animal with the polypeptide having the amino acid sequence corresponding to SEQ ID NO:7. (Hereinafter, this particular antibody is referred to as "anti-DIV6902".) A specific technique for producing and isolating anti-DIV6902 pAB is described in the Example section included herein, but the skilled artisan will recognize that the production and isolating of anti-DIV6902 pAB, or any other antibody of the present invention, is not limited to that specific technique.

In other embodiments, the antibody of the present invention is raised in a host against one or more polypeptides having an amino acid sequence that is a conservative variant of the sequence corresponding to SEQ ID NO:5 or SEQ ID NO:7. In some other embodiments, the antibody of the present invention is raised in a host against any one or more polypeptides having an amino acid sequence corresponding to the sequence of SEQ ID NO:3, SEQ ID NO:4, SEQ ID NO:6, SEQ ID NO:8 or SEQ ID NO:9, or one or more polypeptides having an amino acid sequence that is a conservative variant of any of those sequences.

In another embodiment, the antibody of the present invention is an antibody that specifically binds one or more the polypeptide having the amino acid sequence corresponding to SEQ ID NO:3, SEQ ID NO:4, SEQ ID NO:5, SEQ ID NO:6, SEQ ID NO:7, SEQ ID NO:8, or SEQ ID NO:9, or antigenic portions thereof.

In yet other embodiments, the antibody of the present invention specifically binds one or more polypeptides having an amino acid sequence that is a conservative variant of the sequence corresponding to SEQ ID NO:5 or SEQ ID NO:7. In some other embodiments, the antibody of the present invention specifically binds one or more polypeptides having an amino acid sequence corresponding to the sequence of SEQ ID NO:3, SEQ ID NO:4, SEQ ID NO:5, SEQ ID NO:6, SEQ ID NO:7, SEQ ID NO:8, or SEQ ID NO:9, or one or more polypeptides having an amino acid sequence that is a conservative variant of any of those sequences.

It is also to be understood that the antibodies of the invention may be polyclonal or monoclonal antibodies, single chain antibodies (scFv), chimeric antibodies, and fragments thereof. Monoclonal antibodies that are specific for the polypeptide of interest may be obtained and purified, for example, by preparing cell lines that generate antibodies having the desired specificity to the polypeptide of interest. Cell lines of this kind may be derived from cells of a particular type (e.g., spleen cells) that are isolated from a host animal that had previously been immunized with the polypeptide as described before. In such a case, these cells could then be immortalized, for example, by fusing them with myeloma cells by carrying out any one of a variety of fusion techniques known to the skilled artisan. In one exemplary technique, the cells from the immunized host animal are co-incubated with their fusion partner, e.g., the myeloma cells, in the presence of a detergent for a short period of time before being plated on a medium that supports the growth of hybrid cells (but not the myeloma fusion partner). Such selection may be achieved, for example, by using hypoxanthine, aminopterin, and thymidine (HAT). When hybrid cells emerge during selection, in perhaps one or two weeks after commencing the selection process, single hybrid colonies (and their supernatants) are tested for their ability to bind the polypeptide or polypeptides against which the host animal was immunized. Hybrid colonies having the most optimal binding specificity would represent the best candidates from which monoclonal antibodies may be isolated. These monoclonal antibodies, for example, may be isolated directly from the supernatant (i.e., medium) in which these colonies are grown by employing any one of a variety techniques known to the skilled artisan.

The antibodies of the invention also may be a single chain antibody (scFv), or an antigen binding fragment of an antibody. Antigen-binding fragments of antibodies are a portion of an intact antibody comprising the antigen binding site or variable region of an intact antibody, wherein the portion is free of the constant heavy chain domains of the Fc region of the intact antibody. Examples of antibody fragments include Fab, Fab', Fab'-SH, $F(ab')_2$ and $F_v$ fragments. In addition to production and purification from animals or mammalian cells, antibodies, antibody fragments, or non-antibody scaffolds can be selected based upon various in vitro technologies, including phage display, ribosomal display or bacterial display.

Antibodies, including secondary antibodies, may be labeled with any type of label known in the art, including, for example, fluorescent, chemiluminescent, radioactive, enzymes, colloidal particles, radioisotopes and bioluminescent labels. In various embodiments of the invention, the one or more of the antibodies of the invention are labeled with an enzyme, a colloidal particle, a radionuclide or a fluorophor. The particulate label can be, for example, a colored latex particle, dye sol, or gold sol conjugated to an antibody.

Methods, Devices and Kits of the Invention

Devices and Kits of the Invention

The present invention, in one aspect, is a device for the detection of whipworm infection in a mammal, such as a canine, feline, porcine, bovine, or human, for example. The device is arranged to aid in the detection of the presence or absence of whipworm antigen in a sample from a mammal that may also be infected with one or more other worm parasites, including hookworm, roundworm, and heartworm.

In one aspect, the device includes a solid support, wherein one or more antibodies of the invention are immobilized on the solid support. The solid support may be, but is not limited to being, the inner, bottom surface of a well of a microtiter plate or a substrate that is included as part of a lateral flow device, for example. An exemplary microtiter plate is an Immulon 1B 96-well plate (which is commercially available from Thermo Scientific of Milford, Mass.), but it is to be understood that the skilled artisan will recognize that a large variety of other microtiter plates that are not the Immulon 1B 96-well plate allow for the immobilization of antibodies thereon, and therefore would be suitable for providing the solid support of the present invention.

An exemplary lateral flow device is the lateral flow device that is described in U.S. Pat. No. 5,726,010, which is incorporated herein by reference in its entirety. The device for performing a lateral flow assay may be a SNAP® device, which is commercially available from IDEXX Laboratories, Inc. of Westbrook, Me. However, it is to be understood that the skilled artisan will recognize that a large variety of other lateral flow devices that are not SNAP® devices or described by U.S. Pat. No. 5,726,010 allow for the immobilization of an antibody thereon, and therefore would be suitable for being used as the device of the present invention. These devices can include, for example, lateral flow devices that use colloidal gold technology.

Antibodies used in the device of the invention may be immobilized on the solid support by any methodology known in the art, including, for example, covalently or non-covalently, directly or indirectly, attaching the antibodies to the solid support. Therefore, while these antibodies may be attached to the solid support by physical adsorption (i.e., without the use of chemical linkers), it is also true that these antibodies may be immobilized to the solid support by any chemical binding (i.e., with the use of chemical linkers) method readily known to one of skill in the art.

It is also to be understood that the solid support may be any suitable material for the immobilization of the antibodies of the invention. For example, the solid support may be beads, particles, tubes, wells, probes, dipsticks, pipette tips, slides, fibers, membranes, papers, natural and modified celluloses, polyacrylamides, agaroses, glass, polypropylene, polyethylene, polystyrene, dextran, nylon, amylases, plastics, magnetite or any other suitable material readily known to one of skill in the art.

The device optionally may include one or more labeled antigen capture reagents that may be mixed with a sample from a mammal prior to application to a device of the invention. When the labeled capture antigen reagent is included, the labeled antigen capture reagent may or may not be deposited or dried on a solid surface of the device. "Antigen capture reagent" refers to any compound that is specific for the antigen or antigens of interest. The labeled antigen capture reagent, whether added to the mammalian sample or pre-deposited on the device, may be, for example, a labeled antibody specific for a whipworm antigen, including, but not limited to, the antibodies of the present invention. In one example, anti-DIV6901 pAB or anti-DIV6902 pAB conjugated with horseradish peroxidase may be used as a labeled antigen capture reagent.

The device also may optionally include a liquid reagent that transports (such as when the device is a SNAP® device, for example), or otherwise facilitates removal of (such as when the device includes a microtiter plate, for example), unbound material (e.g., unreacted portions of the mammalian sample, such as, for example, unreacted portions of fecal extract, and unbound antigen capture reagent) away from the reaction zone (solid phase). The liquid reagent may be a wash reagent and serve only to remove unbound material from the reaction zone, or it may include a detector reagent and serve to both remove unbound material and facilitate antigen detection. For example, in the case of an antigen capture reagent conjugated to an enzyme, the detector reagent includes a substrate that produces a detectable signal upon reaction with the enzyme-antibody conjugate at the reaction zone (solid phase). Alternatively, in the case of a labeled antigen capture reagent conjugated to a radioactive, fluorescent, or light-absorbing molecule, the liquid reagent acts merely as a wash solution facilitating detection of complex formation at the reactive zone by washing away unbound labeled reagent.

The liquid reagent may further include a limited quantity of an "inhibitor", i.e., a substance that blocks the development of the detectable end product. A limited quantity is defined as being an amount of inhibitor sufficient to block end product development until most or all excess, unbound material is transported away from the second region, at which time detectable end product is produced.

The device of the present invention may also include various binding reagents immobilized at locations distinct from the antigen capture reagent or reagents. For example, an immunoreagent (an antibody, antigen or polypeptide) that recognizes a species-specific (e.g., whipworm-specific) antibody portion of a labeled antibody or antigen capture reagent, or an enzyme portion of an enzyme-labeled reagent, can be included as a positive control to assess the viability of the reagents within the device. For example, a positive control may be an anti-horseradish peroxidase antibody that has been raised in, for example, goat or mouse. Additionally, a reagent, e.g., an antibody, isolated from a non-immune member of the species from which the antibody portion of the antigen-antibody complex was derived can be included as a negative control to assess the specificity of immunocomplex (i.e., antigen-antibody complex) formation.

In addition to being designed to detect whipworm in a mammalian sample, the device of the invention optionally may be designed to allow one or more other diagnostic tests to be performed. For example, the solid support may also include reagents for the detection of one or more non-whipworm worm parasites, one or more non-worm parasites, one or more viruses, one or more fungi, or one or more bacteria. The reagents for the detection of one or more non-whipworm worm parasites, one or more non-worm parasites, one or more viruses, one or more fungi, or one or more bacteria may be, for example, one or more antibodies or one or more antigens recognized by antibodies specific for one or more non-whipworm worm parasites, one or more non-worm parasites, one or more viruses, one or more fungi, or one or more bacteria.

Figure 6B:
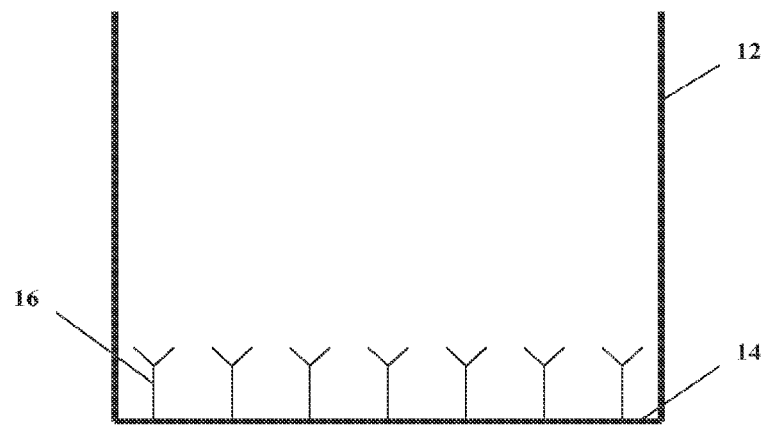
FIG. 6B shows a close up of a single well of the plate of FIG. 6A with a specific antibody of the present invention immobilized thereto.

In one embodiment, which is shown in FIGS. 6A and 6B, the device of the present invention is a microtiter plate 10 that includes a plurality of wells 12, wherein each well 12 includes a solid support 14 having anti-DIV6901 pAB and/or anti-DIV6902 pAB (these antibodies are generally represented as element 16 in FIGS. 6A and 6B) immobilized thereupon.

The plate 10 may be used in conjunction with a method of the present invention to detect whipworm in a mammalian sample. Specifically, a whipworm infection may be diagnosed in a mammal by detecting one or more whipworm antigens with the anti-DIV6901 pAB and/or anti-DIV6902 that is immobilized on the solid support 14. In one embodiment, the antigens that are detected are whipworm coproantigens. "Whipworm coproantigens" are any product or products of whipworm that are present in a fecal sample and that can specifically and stably bind to the anti-DIV6901 pAB and/or the anti-DIV6902 pAB. Whipworm coproantigens therefore may be whole whipworm, whipworm eggs, whipworm fragments, or products secreted, excreted or shed from whipworm or a combination thereof. Whipworm coproantigens further include the polypeptides of the present invention, such as the polypeptides having an amino acid sequence corresponding to SEQ ID NO:3 through SEQ ID NO:9, polypeptides having an amino acid sequence that is a conservative variant of those sequences, and/or antigenic fragments of any such polypeptides, for example.

The invention further includes assay kits (e.g., articles of manufacture) for detecting whipworm in a mammalian sample. A kit therefore may include one or more devices and/or compositions of the present invention. For example, the kit may include anti-whipworm antibodies and means for determining binding of the antibodies to whipworm antigens in the sample. In one particular example, such a kit includes the device having an immobilized anti-whipworm antibody, such as anti-DIV6901 pAB or anti-DIV6902 pAB, for example, one or more antigen capture reagents (e.g., a non-immobilized labeled antigen capture reagent and an immobilized antigen capture reagent) and wash reagent, as well as detector reagent and positive and negative control reagents, if desired or appropriate. Other components such as buffers, controls, and the like, known to those of ordinary skill in art, may be included in such test kits. The relative amounts of the various reagents can be varied, to provide for concentrations in solution of the reagents that substantially optimize the sensitivity of the assay. Particularly, the reagents can be provided as dry powders, usually lyophilized, which on dissolution will provide for a reagent solution having the appropriate concentrations for combining with a sample. The present kit may further include instructions for carrying out one or more methods of the present invention, including instructions for using any device and/or composition of the present invention that is included with the kit.

Methods of the Invention

The present invention further includes methods for using one or more of the devices, kits and/or compositions of the present invention to detect the presence or absence of whipworm in a sample. The methods therefore may be carried out to detect the presence or absence of whipworm in a sample, such as, for example, a fecal sample, that is obtained from a mammal, including, but not limited to, a canine, feline, porcine, bovine or human. Further, the methods may be carried out to detect *Trichuris* and/or *Trichocephalus*, such as *Trichuris vulpis, Trichuris campanula, Trichuris serrata, Trichuris suis, Trichuris trichiura, Trichuris discolor* and *Trichocephalus trichiuris*, for example. These methods further are useful for confirming such presence or absence of whipworm in a sample even when that sample includes one or more products derived from other worm species, including one or more products from hookworm, roundworm, and/or heartworm.

In the methods of the present invention, detection of whipworm may be accomplished by detecting the presence or absence of one or more whipworm antigens, such as the polypeptides having an amino acid sequence corresponding to SEQ ID NO:3 through SEQ ID NO:9, as well as antigenic fragments and/or conservative variants of those sequences, for example. When the sample under test for whipworm is feces, the soluble portion of the feces may be collected by any protocol known in art. For example, in addition to the specific protocol described in the Example section herein, the soluble portions of the sample generally may be collected by using filtration, extraction, centrifugation, or simple mixing followed by gravimetric settling. The skilled artisan will recognize that there are a variety of ways of extracting and preparing non-fecal samples from a mammal as well. For example, the sample may be obtained by swabbing the mammal, such as the oral cavity of the mammal, for example. As yet another example, tissue sections, including tissue from small intestine, large intestine, cecum, colon, rectum, or another tissue of the gastrointestinal tract, may be obtained by biopsy.

The methods include contacting the mammalian sample with one or more antibodies specific for one or more whipworm antigens under conditions that allow an antigen/antibody complex, i.e., an immunocomplex, to form. That is, an antibody specifically binds to a whipworm antigen present in the sample. The skilled artisan is familiar with assays and conditions that may be used to detect such antigen/antibody complex binding. For example, the antigen/antibody complex may be detected using a secondary antibody that binds to the antigen/antibody complex. The formation of a complex between whipworm antigen and anti-whipworm antibodies in the sample may be detected using any suitable method known in the art.

Further, the relative amount of antibody-antigen complexes that are formed in one particular reaction may be measured with respect to those formed in any other reaction by any methodology known in the art for achieving that goal. When it is determined that a sample under test has more antibody-antigen complexes than does a control sample, it can be concluded that whipworm is present in the test sample. When this is true, it may be concluded that the mammal from which the test sample was obtained harbors an intestinal whipworm infection. Either one or both of the conclusions that whipworm is present in the test sample and that the mammal being tested harbors an intestinal whipworm infection may be made by a clinician at a diagnostic service provider or by a caregiver of the mammal, such as the mammal's veterinarian, for example. When a caregiver of a mammal determines (or is otherwise informed that) a mammal harbors a whipworm infection, the caregiver may then subject the mammal to a course of treatment that is optimally designed to rid the mammal of whipworm specifically, rather than of a parasitic nematode infection generally. In addition, humans who may come in contact with the infested animal or its excretions may be advised to take precautions against acquiring the parasite. Further, the present invention can be used to confirm that any animal that has received treatment for a whipworm infection has been rid of that infection.

The steps of the method of the present invention may include applying a mammalian sample to a device of the invention, which includes an immobilized antibody specific for one or more whipworm antigens, and detecting the presence or absence of the whipworm antigen in the sample. Antibodies specific for antigens of whipworms may be directly or indirectly attached to a solid support or a substrate such as a microtiter well, antibody-immobilizing portion of a SNAP® device, magnetic bead, non-magnetic bead, column, matrix, membrane, fibrous mat composed of synthetic or natural fibers (e.g., glass or cellulose-based materials or thermoplastic polymers, such as, polyethylene, polypropylene, or polyester), sintered structure composed of particulate materials (e.g., glass or various thermoplastic polymers), or cast membrane film composed of nitrocellulose, nylon, polysulfone or the like (generally synthetic in nature). All of these substrate materials may be used in suitable shapes, such as films, sheets, or plates, or they may be coated onto or bonded or laminated to appropriate inert carriers, such as paper, glass, plastic films, or fabrics. Suitable methods for immobilizing peptides on solid phases include ionic, hydrophobic, covalent interactions and the like.

The methods of the present invention do not require the use of solid phases or substrates, however. The skilled artisan will recognize that there are a number of ways that the present method may be carried out to detect the presence or absence of whipworm without involving the use of solid phases or substrates. In just one example, immunoprecipitation methods that do not require the use of solid phases or substrates may be carried out.

In some embodiments of the invention, the antigen/antibody complex is detected when an indicator reagent, such as an enzyme conjugate, which is bound to the antibody, catalyzes a detectable reaction. Optionally, an indicator reagent including a signal generating compound may be applied to the antigen/antibody complex under conditions that allow formation of a detectable antigen/antibody/indicator complex. Optionally, the antibody may be labeled with an indicator reagent prior to the formation of an antigen/antibody complex.

The formation of an antigen/antibody complex or an antigen/antibody/indicator complex in some of the methods of the present invention specifically may be detected by radiometric, colorimetric, fluorometric, photometric, size-separation, or precipitation methods. Detection of an antigen/antibody complex also may be accomplished by the addition of a secondary antibody that is coupled to an indicator reagent including a signal generating compound. Indicator reagents including signal generating compounds (labels) associated with a polypeptide/antibody complex may be detected using the methods described above and may include chromogenic agents, catalysts such as enzyme conjugates, fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors, magnetic particles, and the like. Examples of enzyme conjugates include alkaline phosphatase, horseradish peroxidase, beta-galactosidase, and the like. The selection of a particular label is not critical, but it will be capable of producing a signal either by itself or in conjunction with one or more additional substances.

Methods of the invention include, but are not limited to those based on competition, direct reaction or sandwich-type assays, including, but not limited to ELISA, RIA, immunofluorescent assays (IFA), hemagglutination (HA), fluorescence polarization immunoassay (FPIA), and microtiter plate assays (i.e., any assay done in one or more wells of a microtiter plate). One assay of the invention includes a reversible flow chromatographic binding assay, which may be performed, for example, by using a SNAP® device. See U.S. Pat. No. 5,726,010.

In some embodiments, the method of the invention facilitates sandwich or competition-type specific binding assays. In a sandwich assay, antigen capture reagents are immobilized in a reactive zone. These antigen capture reagents may specifically bind to antigens in the sample being tested for whipworm. Following binding of the antigen from the sample, the antigen capture reagent/antigen complex is detected by any suitable method. For example, the complex may be reacted with labeled specific binding reagents (e.g., an enzyme-antibody conjugate) and antigen detected (e.g., upon reaction with substrate).

In other embodiments of the method of the present invention, a competition assay is performed. In a competition assay, antigen capture reagents are immobilized at the reactive zone and are contacted simultaneously with antigen from a sample and labeled antigen (e.g., an antigen-enzyme conjugate). The amount of label detected at the reactive zone is inversely proportional to the amount of antigen in the sample.

In some embodiments of the method, antibodies specific for a whipworm antigen or antigens are attached to a solid phase or substrate. A sample potentially including an antigen from whipworm is added to the substrate. Antibodies that specifically bind whipworm are added. The antibodies may be the same antibodies used on the solid phase or they may be from a different source or species. Further, these antibodies may be linked to an indicator reagent, such as an enzyme conjugate. Wash steps may be performed prior to each addition. A chromophore or enzyme substrate may be added and color may be allowed to develop. The color reaction may be stopped and the color may be quantified using, for example, a spectrophotometer, and/or the color may be subjectively assessed by the human eye.

In other embodiments of the method, antibodies specific for a whipworm antigen or antigens are attached to a solid phase or substrate. A sample potentially including a whipworm antigen is added to the substrate. Second anti-species antibodies that specifically bind antigens of whipworms are added. These second antibodies are from a different species than are the solid phase antibodies. Third anti-species antibodies that specifically bind the second antibodies and that do not specifically bind the solid phase antibodies are added. The third antibodies may include an indicator reagent, such as an enzyme conjugate. Wash steps may be performed prior to each addition. A chromophore or enzyme substrate may added and color may be allowed to develop. The color reaction may be stopped and the color may be quantified using, for example, a spectrophotometer, and/or the color may be subjectively assessed by the human eye.

In a specific example, the method of the present invention is performed in conjunction with a device that is a lateral flow assay device by adding a prepared mammalian sample to a flow matrix of the device at a first region (a sample application zone). The prepared sample is carried in a fluid flow path by capillary action to a second region of the flow matrix where a particulate label capable of binding and forming a first complex with an antigen in the sample exists. The particulate label can be, e.g., a colored latex particle, dye sol, or gold sol conjugated to an antibody specific for a whipworm antigen. The first complex is carried to a third region of the flow matrix where an antibody that specifically binds a whipworm antigen is immobilized at a distinct location. A second complex is formed between the immobilized antibody and the first complex. The particulate label that is part of the second complex can be directly visualized by the human eye.

Whipworm antibody may be an immobilized antigen capture reagent in a reaction zone (solid phase). A second antigen capture reagent, i.e., a second whipworm antibody that has been conjugated to a label, either may be added to the sample before the sample is added to the device, or the second antigen capture reagent can be incorporated into the device. For example, the labeled antigen capture reagent may be deposited and dried on a fluid flow path that provides fluid communication between a sample application zone and the solid phase. Contact of the labeled antigen capture reagent with the test sample can result in dissolution of the labeled antigen capture reagent.

In one embodiment of the method of the present invention, whipworm antigen is detected by ELISA. Specific examples of the ELISA method of the present invention is described in the Example section included herein. Although the present invention is described with respect to those specific ELISA methods, however, it is to be understood that those of ordinary skill in the art will recognize that alternative, additional or substitute ELISA steps may be used without deviating from the basic goal achieved through this method of the invention.

In another embodiment of the present invention, whipworm antigen is detected by using a lateral flow device, such as a SNAP® device, for example.

Further, the methods of the invention for detection of whipworm infection can be combined with other diagnostic assays to detect the presence of other organisms or conditions. For example, assays of the invention can be combined with reagents that detect one or more non-whipworm worm fecal parasites, one or more non-worm fecal parasites, one or more viruses, one or more fungi, one or more bacteria, one or more blood-borne parasites or occult blood or a combination thereof. By providing two or more unique binding sites in a single assay device (such as, for example, two unique spots on a SNAP® assay device), the present invention allows for detection of two or more organisms from a single sample. In one embodiment, there are three unique spots for detection of past or present infection or infestation from three organisms (the spots being either antigen or antibody binding reagents) from a single sample (i.e., the same individual sample is exposed to the three capture reagents on a single device). In yet another embodiment, there are four unique spots for detection of past or present infection or infestation from four organisms (the spots being either antigen or antibody binding reagents) from a single sample (i.e., the same individual sample is exposed to the four capture reagents on a single device. It is to be understood, however, that the same device may include more than four unique spots and/or allow for the detection of more than four organisms.

The reagents for the detection of one or more non-whipworm worm parasites, one or more non-worm parasites, one or more viruses, one or more fungi, or one or more bacteria may be, for example, one or more antibodies or one or more antigens recognized by antibodies specific for one or more non-whipworm worm parasites, one or more non-worm parasites, one or more viruses, one or more fungi, or one or more bacteria.

When a device of the present invention includes reagents for the specific detection of hookworm and reagents for the specific detection roundworm, for example, in addition to the reagents for detecting whipworm, the method of the present invention may involve using that device for the additional purpose or purposes of determining whether the sample that is being tested for whipworm also includes hookworm and/or roundworm. In this arrangement, therefore, the method/device of the present invention would not only be able to specifically confirm that whipworm is present in or absent from any particular test sample, but it would also be useful for specifically confirming that the sample includes or does not include any antigen of hookworm and/or any antigen of roundworm. The capability to specifically detect whipworm and one or more other organisms by applying a single sample to the device of the invention would be useful to the caregiver of the animal from which the sample under test was obtained. A caregiver who learns that a sample includes both whipworm and roundworm, but not hookworm, for example, could use that knowledge to treat the mammal from which the sample was taken specifically for whipworm by administering to that mammal a drug optimally effective against whipworm and a second drug optimally effective against roundworm. Absent such knowledge, the caregiver may, for example, otherwise treat the mammal with a drug that is optimally effective against only whipworm, only roundworm, or neither whipworm nor roundworm (in such cases, the mammal would be at risk of receiving suboptimal treatment). In addition, humans who may come in contact with the infested animal or its excretions may be advised to take precautions against acquiring the parasite or parasites. In this context, it is important to determine the worm species with high specificity, as some helminths, such as roundworms and hookworms, can cause significant disease (i.e., larva migrans, severe enteritis or allergic reactions) in humans, while it is generally accepted that whipworm does not play a zoonotic role of importance in humans.

The method further may optionally include using one or more nucleic acids from whipworm, including, but not limited to, the nucleic acids of the present invention, to determine the presence or absence of whipworm in a mammalian sample. Such use of these nucleic acids for determining the presence of whipworm may be carried out before, after or concomitantly with the carrying out of any other aspects of the method, including the detection of whipworm by antibody. Therefore, in one aspect, after whipworm is detected or not detected in a particular sample and the mammal from which the sample was obtained is diagnosed as either having or not having a whipworm infection, the sample (or a later-obtained sample from the diagnosed mammal) may be tested for the presence or absence of any one or more of the nucleic acids, including any one or more nucleic acids of the invention. Anyone failing to detect whipworm in a particular mammal by using one or more nucleic acids (after the whipworm had been detected by using one or more antibodies) would need to take into consideration the possibility that the antibodies had detected whipworm antigen prior to the appearance of detectable whipworm nucleic acid in the sample. In such an instance, the mammal's caregiver may elect to ignore the observation that the nucleic acid had failed to detect the whipworm and proceed with treating the mammal specifically for whipworm infection based on the observation that the antibodies had in fact detected whipworm. In another aspect, the nucleic acids are used to determine the presence or absence of whipworm in a particular mammal, and then the presence or absence of whipworm is further evaluated by using the antibodies of the present invention. Detection of one or more whipworm nucleic acids may be carried out by using any nucleic acid detection techniques known to the skilled artisan. For example, such detection may be carried out by performing a PCR-based technique, such as, but limited to, for example, a real-time PCR-based technique. Exemplary PCR-based techniques are described in, e.g., *PCR Protocols (Methods in Molecular Biology)*, 2$^{nd}$ ed., Bartlett and Stirling, eds., Humana Press (2003); and Sambrook and Russell, *Molecular Cloning: A Laboratory Manual*, Cold Spring Harbor Laboratory Press (2001); each one of which is incorporated herein by reference in its entirety.

The present invention is specifically described with reference to certain specific Examples; however, it is not to be construed as being limited thereto.

EXAMPLES

Unless otherwise indicated, the following materials and techniques were used to generate data described in one or more of Examples 1-5 as described below.

Polyclonal antibody preparation. The polyclonal antibodies "anti-DIV6901 pAB" (IgG) and "anti-DIV6902 pAB" were raised separately in rabbit against a polypeptide having amino acid sequence corresponding to SEQ ID NO:5 and SEQ ID NO:7, respectively, and purified from serum by using standard methods. Briefly, in the case of anti-DIV6901 pAB, nucleotides 89 through 1147 of SEQ ID NO:1 were cloned in-frame into an expression vector (D8223, which is a derivative of pUC19) to create the plasmid D9073. Specifically, the 353 amino acids of SEQ ID NO:5 that follow the methionine residue at the N-terminus of that sequence correspond to a portion of SEQ ID NO:3 and are encoded for by the cloned portion of SEQ ID NO:1. In the D9073 plasmid, the N-terminal methionine residue was encoded for by vector sequence at the junction of that plasmid where the vector was ligated to the cloned sequence from SEQ ID NO:1.

DNA sequence encoding SEQ ID NO:5 was then cleaved from the D9073 plasmid by restriction exonuclease digestion (NdeI and BamHI) and purified. This purified sequence was then ligated to linearized expression vector, pET28a, and the resulting circular construct (ptDX233::DIV6901) was transformed into *E. coli* cells. (The complete sequence of the insert was confirmed by DNA sequence analysis.) Expression of His-tagged fusion protein was induced by addition of 1 mM IPTG to cultures of the transformed *E. coli*. Recombinant protein was solubilized in 6 M urea and purified by nickel affinity and ion exchange chromatography. (This recombinant protein is hereinafter is referred to as "rDIV6901".)

In the case of anti-DIV6902 pAB, nucleotides 1 through 1059 of SEQ ID NO:2 were cloned in-frame into an expression vector (D8223, which is a derivative of pUC19) to create the plasmid D9074. Specifically, the 353 amino acids of SEQ ID NO:7 that follow the methionine residue at the N-terminus of that sequence correspond to the entirety of SEQ ID NO:4. In the D9074 plasmid, the N-terminal methionine residue was encoded for by vector sequence at the junction of that plasmid where the vector was ligated to the sequence from SEQ ID NO:2.

DNA sequence encoding SEQ ID NO:7 was then cleaved from the D9074 plasmid by restriction exonuclease digestion and purified. This purified sequence was then ligated to linearized expression vector, pET28a, and the resulting circular construct (ptDX234::DIV6902) was transformed into BL21 (DE3) *E. coli* cells. (The complete sequence of the insert was confirmed by DNA sequence analysis.) Expression of His-tagged fusion protein was induced by addition of 1 mM IPTG to cultures of the transformed *E. coli*. Recombinant protein was solubilized in 6 M urea and purified by nickel affinity and ion exchange chromatography. (This recombinant protein is hereinafter is referred to as "rDIV6902".)

Anti-DIV6901 pAB and anti-DIV6902 pAB were purified from the plasma of the immunized rabbits by isolating IgG antibody by protein G affinity chromatography. The polyclonal antibodies anti-DIV6901 pAB and/or anti-DIV6902 pAB were used in all five Examples described herein.

Infection and anti-helminth treatment of canine and feline animals. Parasitic nematode infection was effected by orally administering about 150-300 larvated eggs of either whipworm (*Trichuris vulpis*), hookworm (*Ancylostoma canium*), or roundworm (*Toxocara canis*) to a healthy canine For Examples 1 and 2, fecal samples were collected from canines known to be naturally infected with heartworm (*Dirofilaria immitis*). Further, for Examples 4 and 5 only, canines were treated at post-infection day 91 with Interceptor® (milbemycin oxime), which is an anthelmintic agent commercially available from Novartis Animal Health Inc. of Basel, Switzerland, according to the manufacturer's protocol. It is well known by those of ordinary skill in the art that Interceptor® is effective for the removal of whipworms (and other parasitic worms) from canines Infection was confirmed by microscopic observation of worm ova in fecal samples obtained from these host animals.

Canine fecal sample preparation. Canine animals known to be free of parasitic worm infection or to be infected with one of either whipworm, hookworm, roundworm or heartworm provided the source of fecal samples. Samples (approximately 1 gram) from fresh, unpreserved canine or feline fecal samples were suspended in 4 ml of diluent solution ("diluent solution" is 0.05 M Tris base; 1 mM EDTA; 0.45% Kathon; 16 mg/ml gentamicin sulfate; 0.05% Tween-20; 40% fetal bovine serum; 10% rabbit serum; and 5% mouse serum). The suspension was centrifuged at 4000 rpm for 20 minutes to produce a first supernatant. The first supernatant was centrifuged at 12000 rpm for 5 minutes to produce a second supernatant, which is referred to herein as "fecal extract".

ELISA assays. Purified anti-DIV6901 pAB (3 µg/ml; 100 µl/well) or purified anti-DIV6902 pAB (3 µg/ml; 100 µl/well) was immobilized by physical adsorption on Immulon 1B 96-well plates overnight at 4° C. The plates were then blocked with 1% BSA in 0.1M Tris pH 7.0 at 4° C. overnight, followed by drying at room temperature. Approximately 100 µl of fecal extract was added to each well and allowed to incubate at room temperature for one hour. The wells were then washed five times with a PBS-Tween-20 solution according to standard methods known to those of ordinary skill in the art. Free anti-DIV6901 pAB or anti-DIV6902 was labeled with horseradish peroxidase (HRP) by using the crosslinker succinimidyl 4-[N-maleimidomethyl]cyclohexane-1-carboxylate (SMCC) to create a first conjugate, and 3 µg/ml of this first conjugate was added to each well having immobilized anti-DIV6901 pAB or anti-DIV6902 pAB. Following a 30-minute incubation period at room temperature, unbound first or second conjugate was washed from the wells by using PBS-Tween-20 solution according to standard methods known to those of ordinary skill in the art. 50 μl of TMBLUE® peroxidase substrate (SeraCare Life Sciences, West Bridgewater, Mass.) was then added to each well and the plates were incubated for 10 minutes at room temperature. After stopping each enzymatic reaction with 0.1% sodium dodecyl sulfate (SDS) following the 10-minute incubation period, the optical density (OD) value of each well of the 96-well plate was measured at A650 by standard spectrophotometric techniques by using an ELISA plate reader to generate an "OD650 value" (or, more simply, an "OD value") for each well. In this arrangement, the OD value obtained for any particular well of the 96-well plate was directly proportional to the amount of specifically bound antigen present in the well.

Example 1

Each one of anti-DIV6901 pAB and anti-DIV6902 pAB specifically binds whipworm in fecal samples obtained from whipworm-infected canines, and neither of these antibodies specifically binds coproantigen of either hookworm, roundworm or heartworm.

Figure 7:
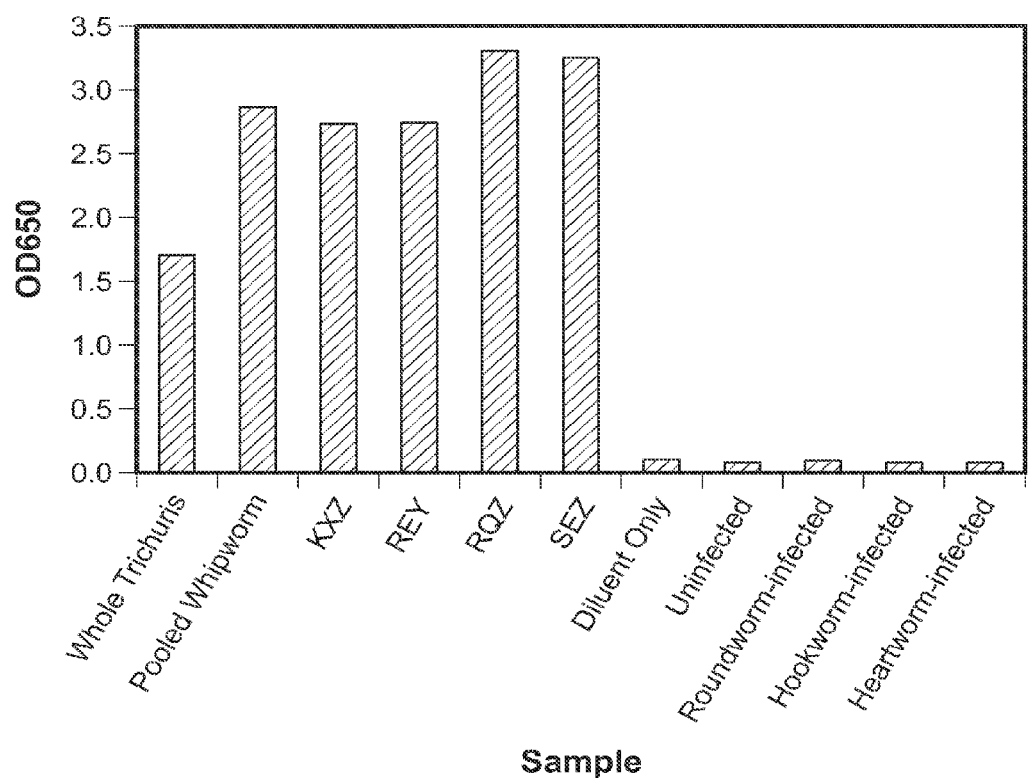
FIG. 7 shows a graph of optical density (OD) values obtained from fecal samples from whipworm-infected canines and from canines infected with either hookworm, roundworm or heartworm by using a first antibody of the present invention and by following the method of the present invention in a first Example.
Figure 8:
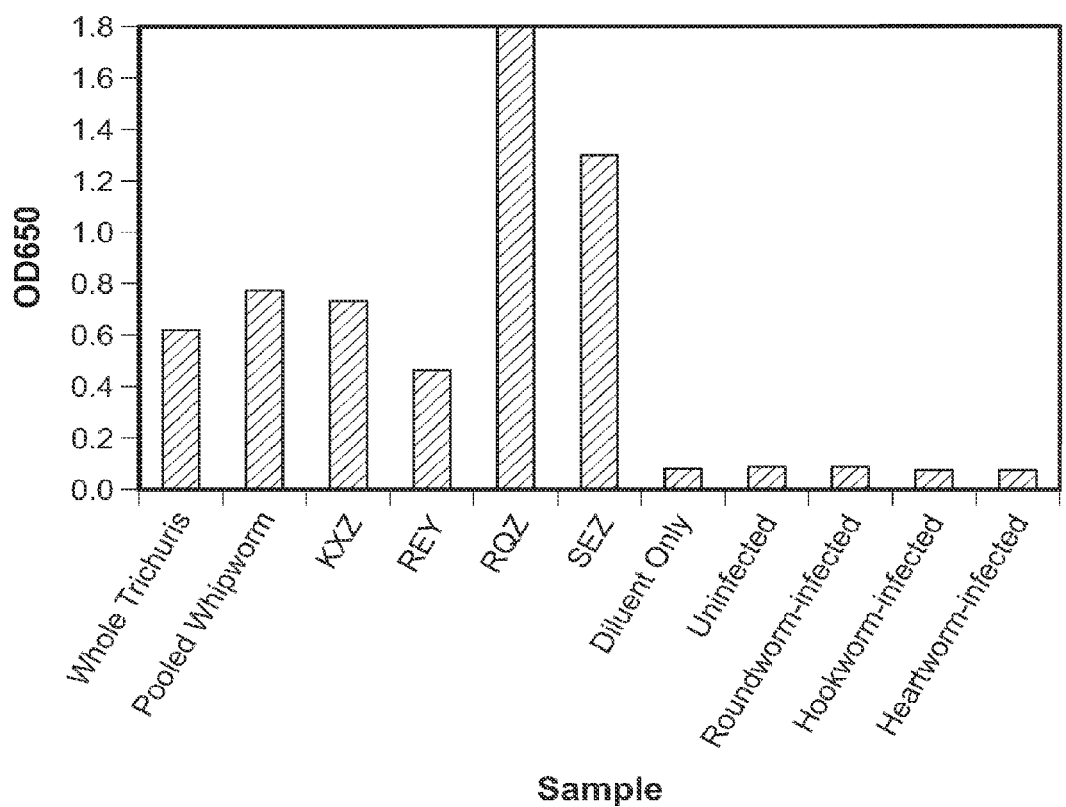
FIG. 8 shows a graph of optical density (OD) values obtained from fecal samples from whipworm-infected canines and from canines infected with either hookworm, roundworm or heartworm by using a second antibody of the present invention and by following the method of the present invention in the first Example.

It was a goal of Example 1 to determine whether anti-DIV6901 pAB and/or anti-DIV6901 pAB specifically binds whipworm coproantigen in canines Measured OD values for fecal samples obtained from individual canines that were known to have a whipworm-infection are shown in FIGS. 7 and 8. Specifically, in each case, these samples correspond to the individual whipworm-infected canines that are identified as "KXZ" (day 73), "REY" (day 85), "RQZ" (day 76), "SEZ" (day 85) and a pooled sample obtained from those whipworm-infected canines (which is identified as "pooled whipworm") in FIGS. 7 and 8. An OD value also was measured for whole extract of *Trichuris vulpis* ("whole *Trichuris*"), which served as a positive control, and from a sample that did not contain any fecal extract ("diluent only"), which served as a negative control. (Specifically, whole extract of *Trichuris vulpis* was prepared as described for whole extract of *Toxocara* in U.S. patent application Ser. No. 11/763,592, assigned to the assignee of the present invention, which is incorporated herein by reference in its entirety.) Further, an OD value was measured for a fecal extract obtained from a canine that did not have a parasitic worm infection ("uninfected"), which also served as a negative control.

As shown in FIG. 7, the measured OD value of the fecal extract obtained from the negative control uninfected and diluent only samples using anti-DIV6901 pAB as the capture and detection antibody was 0.07 and 0.09, respectively. (The average OD value for these negative control samples therefore was 0.08.) The anti-DIV6901 pAB therefore was considered to not have specifically bound antigen in any one of these negative control samples.

Conversely, the measured OD values of the samples obtained from the whipworm-positive canines "KXZ", "REY", "RQZ", "SEZ", and from the pooled extract from those canines using anti-DIV6901 pAB as the capture and detection antibody were 2.85, 2.71, 2.73, 3.29, and 3.24, respectively. These values were about 34 times higher to about 41 times higher than the average OD value measured for the two negative control samples. These data indicate that anti-DIV6901 pAB specifically binds one or more whipworm coproantigens.

Further, as shown in FIG. 8, the measured OD value of the fecal extract obtained from the negative control uninfected and diluent only samples using anti-DIV6902 pAB as the detection antibody was 0.09 and 0.08, respectively. (The average OD value for these negative control samples therefore was 0.09.) The anti-DIV6902 pAB therefore was considered to not have specifically bound antigen in any one of these negative control samples.

Conversely, the measured OD values of the samples obtained from the whipworm-positive canines "KXZ", "REY", "RQZ", "SEZ", and from the pooled extract from those canines using anti-DIV6902 pAB as the capture and detection antibody were 0.73, 0.46, 1.79, 1.29, and 0.77, respectively. These values were about five times higher to about 20 times higher than the average OD value measured for the two negative control samples. These data indicate that anti-DIV6902 pAB specifically binds one or more whipworm coproantigens.

It was another goal of Example 1 to determine whether anti-DIV6901 pAB and/or anti-DIV6902 pAB specifically binds roundworm, hookworm or heartworm coproantigen in canines. As shown in FIGS. 7 and 8, an OD value further was measured for a fecal extract obtained from a canine that was infected with roundworm ("roundworm-infected"), from a canine that was infected with hookworm ("hookworm-infected") and from a canine that was infected with heartworm ("heartworm-infected").

With specific reference being made to FIG. 7, the measured OD values of the samples obtained from the hookworm-infected, roundworm-infected, and heartworm-infected canines using anti-DIV6901 pAB as the capture and detection antibody were 0.08, 0.07 and 0.06, respectively. These values were less than the average OD value measured for the two negative control samples. These data therefore indicate that anti-DIV6901 does not specifically bind any coproantigen from roundworm, hookworm or heartworm.

With specific reference now being made to FIG. 8, the measured OD values of the samples obtained from the hookworm-infected, roundworm-infected, and heartworm-infected canines using anti-DIV6902 pAB as the capture and detection antibody were 0.09, 0.08 and 0.08, respectively. These values were equal to or less than the average OD value measured for the two negative control samples. These data therefore indicate that anti-DIV6903 does not specifically bind any coproantigen from roundworm, hookworm or heartworm.

Example 2

Anti-DIV6901 pAB specifically binds roundworm coproantigen, but does not specifically bind coproantigen from either hookworm, whipworm or heartworm, and specific binding of roundworm coproantigen by anti-DIV6901 pAB produces a colorimetric change that is readily observable to the human eye.

It was a goal of Example 2 to determine whether specific binding between anti-DIV6901 pAB and roundworm coproantigen while the anti-DIV6901 pAB is immobilized on a solid support can produce a colorimetric change that is observable to the human eye.

Figure 9:
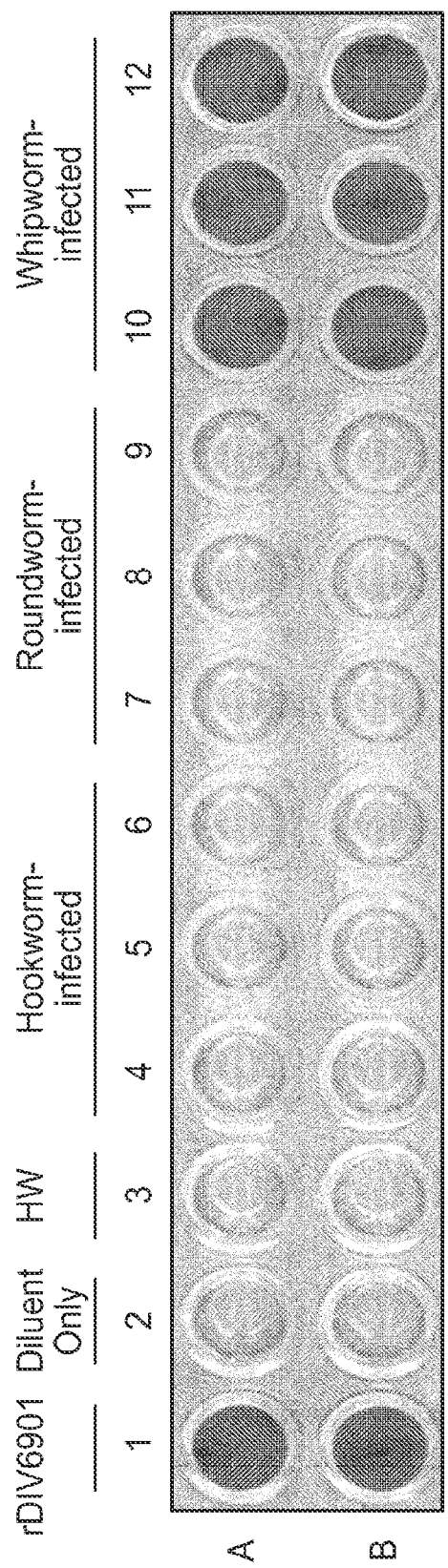
FIG. 9 shows the results of a first ELISA assay, which was carried out by using a microtiter plate and which tested fecal samples from canines infected with either whipworm, hookworm, roundworm or heartworm by following the method of the present invention in a second Example.

Referring to FIG. 9, anti-DIV6901 pAB (3 μg/ml) was immobilized onto the bottom surfaces of wells A1-A12 and B1-B12 of a microtiter plate as described before. Following such immobilization, the A3 and B3 wells were exposed to fecal extract from a heartworm-infected canine (indicated by "HW" in FIG. 9). The A4 and B4 wells were exposed to fecal extract from a first hookworm-infected canine, the A5 and B5 wells were exposed to fecal extract from a second hookworm-infected canine, and the A6 and B6 wells were exposed to fecal extract from a third hookworm-infected canine. The A7 and B7 wells were exposed to fecal extract from a first roundworm-infected canine, the A8 and B8 wells were exposed to fecal extract from a second roundworm-infected canine, and the A9 and B9 wells were exposed to fecal extract from a third roundworm-infected canine. The A10 and B10 wells were exposed to fecal extract from a first whipworm-infected canine, the A11 and B11 wells were exposed to fecal extract from a second whipworm-infected canine, and the A12 and B12 wells were exposed to fecal extract from a third whipworm-infected canine. The A1 and B1 wells were exposed to rDIV6901 (1 µg/ml), and therefore those wells served as positive controls. The A2 and B2 wells were not exposed to any fecal extract or to rDIV6901, and therefore those wells served as negative controls.

Following incubation of all of these wells with TMBLUE® peroxidase substrate and the subsequent addition of the SDS, colorimetric change was visually observed in each one the wells that had been exposed to fecal extract from whipworm-infected canines (A10-A12 and B10-B12), but no colorimetric change was observed in any of the wells that had been exposed to fecal extract from canines infected with either hookworm, roundworm or heartworm.

These data indicate that anti-DIV6901 pAB detects whipworm sufficiently enough to produce a colorimetric change that is robust and readily visible to the human eye. Further, these data indicate that such colorimetric change allows the human eye to readily distinguish whipworm-positive fecal samples from those that do not contain whipworm, including those that include one or more of hookworm, roundworm, or heartworm.

Example 3

When tested by ELISA in a lateral flow format, anti-DIV6901 pAB specifically binds whipworm coproantigen and this specific binding of whipworm coproantigen by anti-DIV6901 pAB produces a colorimetric change that is readily observable to the human eye.

It was a goal of Example 3 to determine whether anti-DIV6901 pAB can be used to capture and detect whipworm coproantigen in a lateral flow ELISA. The lateral flow format that was used was a SNAP® assay device, similar to that which is described in U.S. Pat. No. 5,726,010. Further, the assay was performed generally as described in that same patent. Briefly, among other components, the SNAP® assay device included a sample entry cup, a flow matrix, a sample prefilter pad for removing interfering particulate matter, a specific binding reagent pad, a reactive zone, and an absorbent reservoir. Anti-DIV6901 pAB was immobilized in the form of a small, round spot at the reactive zone by drying (this bound anti-DIV6901 pAB is referred to hereinafter, in this Example only, as the "capture reagent".) The reactive zone was then blocked with BSA. A pooled fecal extract (150 µl) from whipworm-infected canines was mixed with 200 µl (1.0 µg/ml) conjugated anti-DIV6901 pAB (the anti-DIV6901 pAB was affinity-purified before being labeled with HRP as described above; this conjugated anti-DIV6901 pAB is referred to hereinafter, in this Example only, as the "detection reagent"). This mixture added to the sample cup and then was allowed to flow along the flow matrix. While in the flow matrix, the detection reagent specifically bound to whipworm coproantigens present in the fecal extract. The resulting complexes (i.e., those that included the detection reagent and the whipworm coproantigen) were allowed to specifically bind to the immobilized capture reagent at the reaction zone. Flow along the flow matrix was reversed by contacting the absorbent reservoir with the flow matrix. At this time, detector and wash solution migrated into the flow matrix to remove any unbound components and to allow detection of any analyte complexes that were present where the capture reagent was immobilized onto the reaction zone. (This detection step lasted about eight minutes.) Stopping of the detection of the analyte complexes occurred by exposing the analyte complexes to 0.1% azide.

Figure 10:
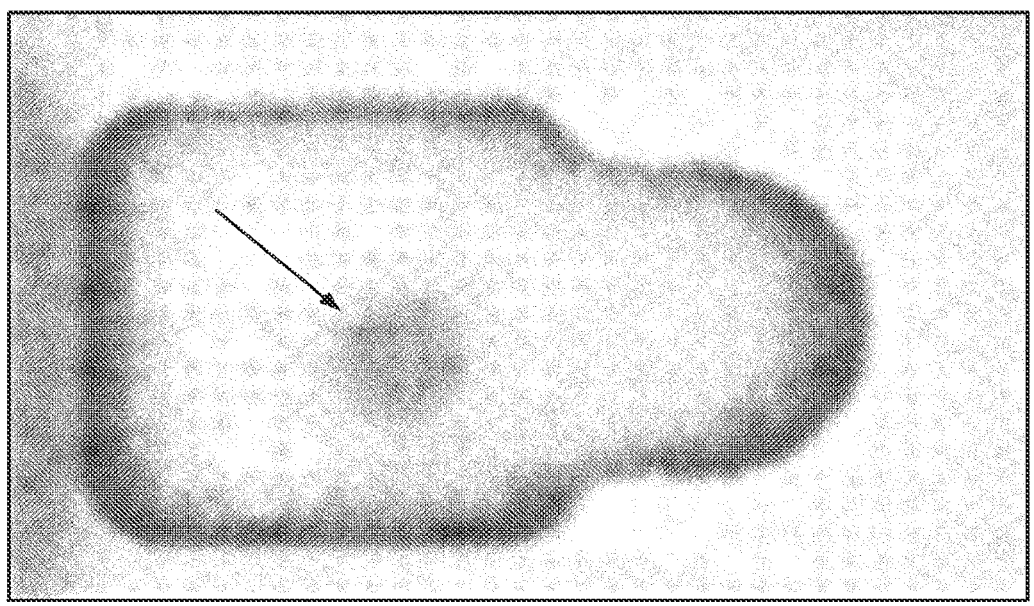
FIG. 10 shows the results of a second ELISA assay, which was carried out by using a lateral flow device and which tested fecal samples from canines infected with whipworm by following the method of the present invention in a third Example.
Figure 11:
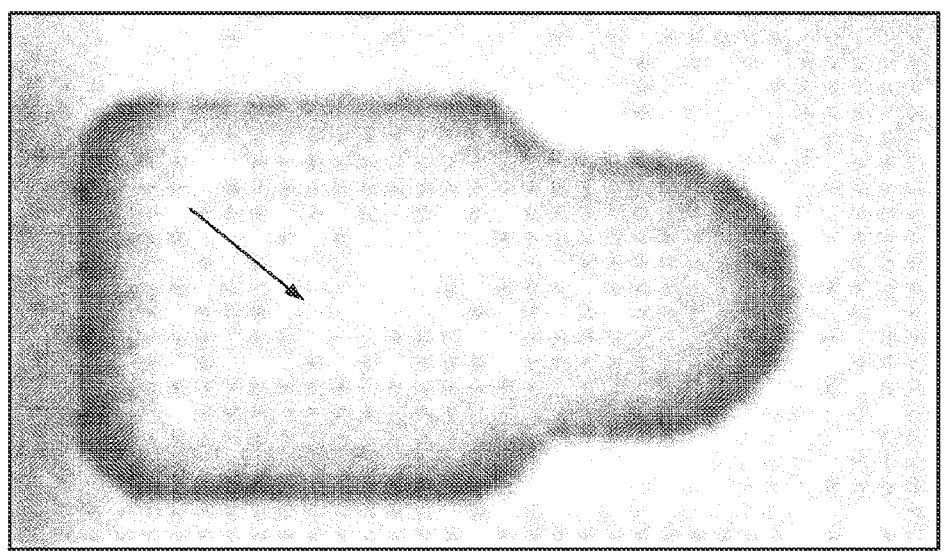
FIG. 11 shows the results of a third ELISA assay, which was carried out by using a lateral flow device and which tested fecal samples from canines that were not infected with whipworm by following the method of the present invention in the third Example.

As shown in FIG. 10, detection of analyte complexes where the capture reagent was immobilized onto the reaction zone was visibly apparent (see the darkened spot indicated by the arrow). In a negative control sample shown in FIG. 11, no analyte complexes were detected where the capture reagent was immobilized onto the reaction zone of a separate device. (The negative control assay was performed exactly as was the whipworm detection assay, with one exception, which was that the fecal extract that was used in the negative control was obtained from a canine that did not harbor a whipworm infection.) These data therefore indicate that anti-DIV6901 pAB can be used in a lateral flow ELISA format to specifically bind whipworm coproantigen. This specific binding is readily visible to the human eye.

Example 4

Anti-DIV6901 pAB detects whipworm coproantigen in some canines as early as 31 days after being infected with whipworm, and anti-DIV6901 pAB does not detect whipworm in feces of canine animals that have had a whipworm infection, but that have been treated for that infection by the time the feces were excreted by the canines.

It was a goal of Example 4 to determine whether anti-DIV6901 pAB can detect whipworm coproantigens in whipworm-infected canines before whipworm ova first appear in the feces of those canines.

Figure 12:
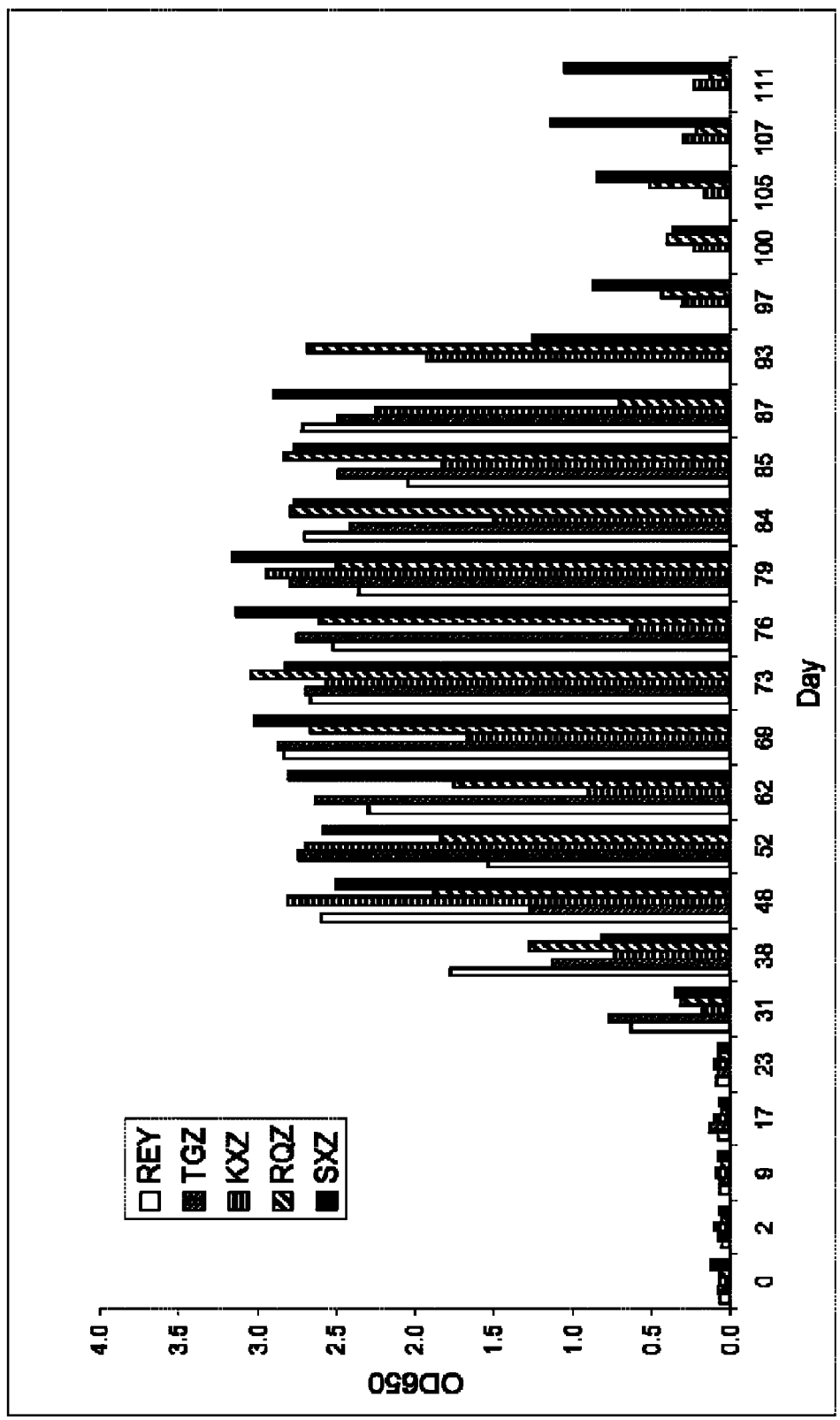
FIG. 12 shows a first graph of OD values obtained from fecal samples from a set of canines that had an active roundworm infection and from fecal samples from those canines after they had been rid of their active roundworm infection by following the method of the present invention in a fourth Example.

OD values measured for fecal samples obtained from a first set of five canines on the day those animals were infected with whipworm ("day 0"), and from the same five canines at day 111 after those animals were infected with whipworm, and for several selected days there between, are shown in FIG. 12. (These five canines are identified as "REY", "TGZ", "KXZ", "RQZ", and "SXZ".) Each one of these whipworm-infected canines was treated with the Interceptor® anthelmintic agent on day 91 of this period as described before. Microscopic observation of each one of these fecal samples confirmed that whipworm ova were substantially present only on day 69, 73, 76, 79, 84, 85, 87 and 93.

Figure 13:
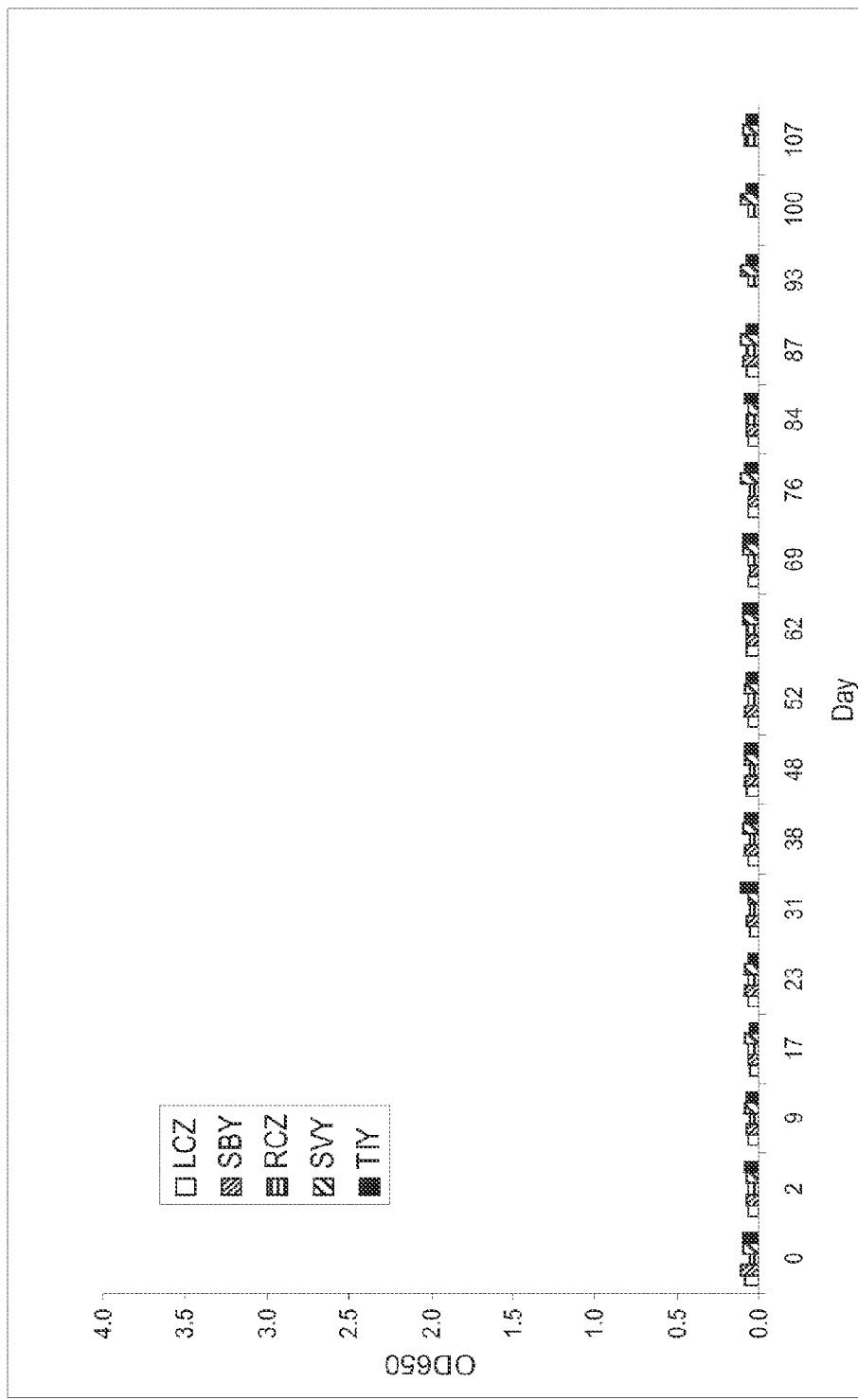
FIG. 13 shows a second graph of OD values obtained from fecal samples from a set of felines that did not have a parasitic worm infection by following the method of the present invention in the fourth Example.

Further, OD values measured for fecal samples obtained from a second set of five canines, which were never infected with whipworm, are shown in FIG. 13. Fecal samples were taken from this second set canines, which are identified as "LCZ", "SBY", RCZ", "SVY" and "TIY", on the day that the whipworm infections were introduced to the first set of canines, on day 111 following those infections, and on several selected days there between. Microscopic observation of the fecal samples from the second set of canines confirmed that each one of the samples taken at day 0 through day 111 was free of whipworm ova.

Referring to FIG. 12, the average of the OD values measured for the fecal samples taken from the first set of canines prior to day 31 was 0.08 (with the highest measured OD value among these samples being 0.13). Referring to FIG. 13, each one of the OD values measured for the fecal samples taken from the second set of canines throughout the test period was equal to or was approximately equal to 0.08 (with the highest measured OD value among these samples being 0.11). Anti-DIV6901 pAB therefore was considered to not have specifically bound antigen in any one of the samples taken from the uninfected canines (i.e., the second set of canines) throughout the test period or from the whipworm-infected canines (i.e., the first set of canines) prior to day 31.

Conversely, referring again to FIG. 12, the OD values for the REY and TGZ canines on day 31 were 0.62 and 0.77, respectively, which were about eight-to-10 times greater than was the average OD value measured for all of the fecal samples from the first set of canines prior to day 31. Further, the OD values for the RQZ and SXZ canines on day 31 were 0.32 and 0.35, respectively, which were more than four times greater than was the average OD value measured for all of the fecal samples prior to day 31. These data indicate that anti-DIV6901 pAB can detect whipworm in canine feces as early as 31 days after the canine becomes infected with whipworm and prior to the first appearance of whipworm ova in those feces.

It was another goal of Example 4 to determine whether anti-DIV6901 pAB detects whipworm in feces of a canine animal that has been treated for a prior whipworm infection.

Referring to FIG. 12, the OD values measured for the fecal samples taken from the first set of canines (i.e., the canines that were infected with whipworm) at days 38 through 93 were many times higher than were the OD values measured for fecal samples from those same canines in the samples taken more than six days following their treatment with the anthelmintic agent. However, the OD values remained above the baselines of measured prior to infection, and above the levels seen in uninfected (FIG. 13) canines. This may indicate incomplete removal of whipworms by the anthelmintic agent, or continued presence of larval whipworms due to the fact that the treatment only affects the adult stage. These data indicate that anti-DIV6901 pAB detects whipworm at sharply reduced levels in feces from a canine that has been treated for a prior whipworm infection.

Example 5

Anti-DIV6902 pAB detects whipworm coproantigen in some canines as early as 52 days after being infected with whipworm, and anti-DIV6902 pAB does not detect whipworm in feces of canine animals that have had a whipworm infection, but that have been rid of that infection by the time the feces were excreted by the canines.

It was a goal of Example 5 to determine whether anti-DIV6902 pAB can detect whipworm coproantigens in whipworm-infected canines before whipworm ova first appear in the feces of those canines. It was another goal of Example 5 to determine whether anti-DIV6902 pAB detects whipworm in feces of a canine animal that has been rid of a prior whipworm infection.

Figure 14:
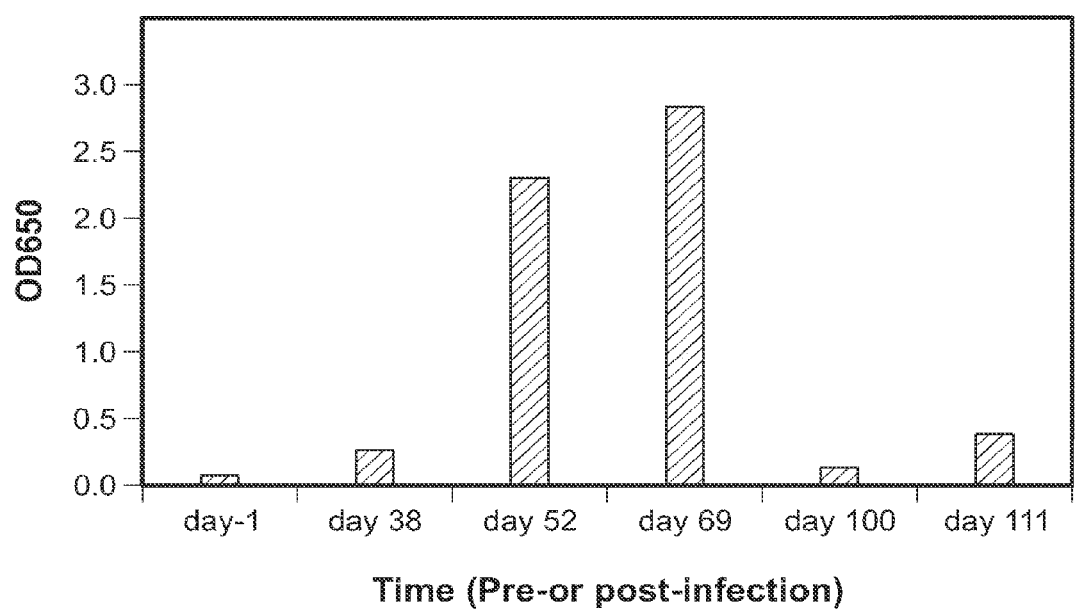
FIG. 14 shows a graph of OD values obtained from fecal samples that were taken from a canine prior to, during, and after the canine had an active roundworm infection by following the method of the present invention in a fifth Example.

OD values measured for fecal samples obtained from an uninfected canine (dog SEZ) one day prior to that animal's infection with whipworm ("day-1") and from the same canine at days 38, 52, 69, 100 and 111 after that animal was infected with whipworm are shown in FIG. 14. This whipworm-infected canine was treated with the Interceptor® anthelmintic agent on day 91 of this period as described before. Microscopic observation of these fecal samples confirmed that each one of the "day-1", "day 38", "day 52", "day 100" and "day 111" samples was substantially free of roundworm ova, and that such ova were abundant in the "day 69" sample.

Referring to FIG. 14, the OD value measured for the fecal sample taken at post-infection day 52 was 2.29, which was almost 30 times greater than was the OD value that was measured for the day-1 sample (0.08). The data shown in FIG. 14 therefore indicate that anti-DIV6902 pAB can detect whipworm in canine feces as early as 52 days after the canine becomes infected with whipworm, and prior to the first appearance of whipworm ova in those feces.

Further, the OD value measured for the fecal sample taken at post-infection day 52 (2.29) was almost 18 times greater than was the OD value that was measured for the day 100 sample (0.13) and was more than five times greater than was the OD value that was measured for the day 111 sample (0.40). The OD value measured for the fecal sample taken at post-infection day 69 (which specifically was 2.83) was more than 20 times greater than was the OD value that was measured for the day 100 sample and was more than seven times greater than was the OD value that was measured for the day 111 sample. The data shown in FIG. 14 therefore further indicate that anti-DIV6902 pAB does not detect whipworm in feces of a canine that has been rid of a prior whipworm infection.

The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

A number of examples to help illustrate the invention have been described. Nevertheless, it will be understood that various modifications may be made without departing from the spirit and scope of the invention. Accordingly, other embodiments are within the scope of the claims appended hereto.

What is claimed is:

1. An isolated antibody wherein the antibody specifically binds to the polypeptide consisting of the amino acid sequence of SEQ ID NO:3, SEQ ID NO:4, SEQ ID NO:5, SEQ ID NO:6, SEQ ID NO:7, SEQ ID NO:8, or SEQ ID NO:9.

2. The isolated antibody of claim 1, wherein the antibody is obtained by immunization with a polypeptide consisting of the amino acid sequence of SEQ ID NO:3, SEQ ID NO:4, SEQ ID NO:5, SEQ ID NO:6, SEQ ID NO:7, SEQ ID NO:8, or SEQ ID NO:9.

3. The isolated antibody of claim 1, wherein the antibody is detectably labeled.

4. The isolated antibody of claim 1, wherein the antibody specifically binds to whipworm antigen in a fecal sample obtained from a whipworm-infected mammal.

5. The isolated antibody of claim 4, wherein the whipworm infected mammal is further infected with one or more of hookworm, roundworm and heartworm and the antibody does not bind to any antigen from the one or more of hookworm, roundworm, or heartworm that may be present in the fecal sample.

6. The isolated antibody of claim 1, wherein the antibody is immobilized on a solid support.

7. The isolated antibody of claim 4, wherein the whipworm is *Trichuris vulpis*.

8. The isolated antibody of claim 5, wherein the hookworm is *Ancylostoma caninum*, the roundworm is *Toxocara canis*, and/or the heartworm is *Dirofilaria immitis*.

9. The isolated antibody of claim 1, wherein the antibody is a single chain antibody, or an antigen binding fragment of an antibody.

10. The isolated antibody of claim 1, wherein the antibody is a polyclonal or monoclonal antibody.

* * * * *